US012752105B2

(12) United States Patent
Beck et al.

(10) Patent No.: US 12,752,105 B2
(45) Date of Patent: Oct. 6, 2026

(54) FATIGUE-RESISTANT ELECTROSTIMULATION LEADS AND METHODS OF USE THEREOF

(71) Applicant: Mainstay Medical Limited, County Dublin (IE)

(72) Inventors: John Beck, Ramsey, MN (US); Jason Skubitz, Arden Hills, MN (US)

(73) Assignee: Mainstay Medical Limited, Dublin (IE)

(*) Notice: Subject to any disclaimer, the term of this patent is extended or adjusted under 35 U.S.C. 154(b) by 393 days.

(21) Appl. No.: 18/330,097

(22) Filed: Jun. 6, 2023

(65) Prior Publication Data

US 2023/0398346 A1 Dec. 14, 2023

Related U.S. Application Data

(60) Provisional application No. 63/366,132, filed on Jun. 9, 2022.

(51) Int. Cl.
*A61N 1/05* (2006.01)
*A61N 1/36* (2006.01)

(52) U.S. Cl.
CPC ....... *A61N 1/0558* (2013.01); *A61N 1/36062* (2017.08)

(58) Field of Classification Search
None
See application file for complete search history.

(56) References Cited

U.S. PATENT DOCUMENTS

| | | |
|---|---|---|
| 1,526,595 A | 2/1925 | George et al. |
| 3,077,884 A | 2/1963 | John et al. |

(Continued)

FOREIGN PATENT DOCUMENTS

| | | |
|---|---|---|
| CN | 1211930 A | 3/1999 |
| CN | 1211930 C | 7/2005 |

(Continued)

OTHER PUBLICATIONS

Airaksinen, et al., Chapter 4. European guidelines for the management of chronic nonspecific low back pain, European spine journal [I: official publication of the European Spine Society, the European Spinal Deformity Society, and the European Section of the Cervical Spine Research Society 15 Suppl 2:S192-300 (2006), http://www.ncbi.nlm.nih.gov/pubmed/16550448.

(Continued)

*Primary Examiner* — Paula J Stice

(74) *Attorney, Agent, or Firm* — Greenberg Traurig, LLP; Christopher C. Bolten; Albert K. Heng

(57) ABSTRACT

A lead for providing neuromuscular electrical stimulation that enhances fatigue-resistance, as well as methods of use thereof, and methods for manufacturing the same, are provided. The lead has a proximal region, a distal region, a fatigue-resistant zone disposed between the proximal region and the distal region, and one or more conductors comprising individual strands that extend from the distal region to the proximal region substantially parallel to a longitudinal axis of the electrostimulation lead outside of the fatigue-resistant zone. The individual strands of one or more conductors are wound in a coiled configuration within the fatigue-resistant zone to enhance fatigue-resistance. Moreover, the fatigue-resistant zone is configured to be disposed at a location within the patient that experiences fracture-inducing shear forces caused by movement of the patient's lower back muscles.

20 Claims, 4 Drawing Sheets

(56) References Cited

U.S. PATENT DOCUMENTS 3,416,534 A 12/1968 Quinn
3,710,777 A 1/1973 Sparks
3,754,555 A 8/1973 Schmitt
3,875,947 A 4/1975 Jula et al.
3,893,463 A 7/1975 Williams
3,902,501 A 9/1975 Citron et al.
3,976,082 A 8/1976 Schmitt
3,999,551 A 12/1976 Spitz et al.
4,010,757 A 3/1977 Jula et al.
4,026,301 A 5/1977 Friedman et al.
4,031,899 A 6/1977 Renirie
4,149,528 A 4/1979 Murphy
4,235,246 A 11/1980 Weiss
4,269,198 A 5/1981 Stokes
4,342,317 A 8/1982 Axelgaard
4,408,609 A 10/1983 Axelgaard
4,418,693 A 12/1983 LeVeen et al.
4,471,777 A 9/1984 McCorkle, Jr.
4,528,984 A 7/1985 Morawetz et al.
4,549,556 A 10/1985 Tarjan et al.
4,574,806 A 3/1986 McCarthy
4,608,986 A 9/1986 Beranek et al.
4,651,751 A * 3/1987 Swendson .............. A61N 1/056 607/122
4,658,835 A 4/1987 Pohndorf
4,696,308 A 9/1987 Meller et al.
4,832,687 A 5/1989 Smith, III
4,863,430 A 9/1989 Klyce et al.
4,917,093 A 4/1990 Dufresne et al.
5,069,680 A 12/1991 Grandjean
5,199,430 A 4/1993 Fang et al.
5,215,088 A 6/1993 Normann et al.
5,273,053 A 12/1993 Pohndorf
5,300,108 A 4/1994 Rebell et al.
5,330,515 A 7/1994 Rutecki et al.
5,376,108 A 12/1994 Collins et al.
5,496,345 A 3/1996 Kieturakis et al.
5,501,452 A 3/1996 Halvorson
5,507,788 A 4/1996 Lieber
5,522,854 A 6/1996 Ideker et al.
5,569,183 A 10/1996 Kieturakis
5,575,797 A 11/1996 Neubauer et al.
5,638,825 A 6/1997 Yamazaki et al.
5,651,781 A 7/1997 Grace
5,733,307 A 3/1998 Dinsdale
5,741,321 A 4/1998 Brennen
5,760,341 A 6/1998 Laske et al.
5,782,841 A 7/1998 Ritz et al.
5,807,234 A 9/1998 Bui et al.
5,873,900 A 2/1999 Maurer et al.
5,897,584 A 4/1999 Herman
5,906,612 A 5/1999 Chinn
5,916,172 A 6/1999 Hodges et al.
5,957,968 A 9/1999 Belden et al.
5,980,515 A 11/1999 Tu
6,104,957 A 8/2000 Alo et al.
6,119,516 A 9/2000 Hock
6,314,325 B1 11/2001 Fitz
6,319,241 B1 11/2001 King et al.
6,324,414 B1 11/2001 Gibbons et al.
6,366,819 B1 4/2002 Stokes
6,381,496 B1 4/2002 Meadows et al.
6,406,421 B1 6/2002 Grandjean et al.
6,451,036 B1 9/2002 Heitzmann et al.
6,473,654 B1 10/2002 Chinn
6,516,227 B1 2/2003 Meadows et al.
6,527,787 B1 3/2003 Fogarty et al.
6,565,594 B1 5/2003 Herweck et al.
6,600,954 B2 7/2003 Cohen et al.
6,600,956 B2 7/2003 Maschino et al.
6,605,094 B1 8/2003 Mann et al.
6,671,557 B1 12/2003 Gliner
6,735,474 B1 5/2004 Loeb et al.
6,839,594 B2 1/2005 Cohen et al.
6,845,271 B2 1/2005 Fang et al.
6,862,479 B1 3/2005 Whitehurst et al.
6,971,393 B1 12/2005 Mamo et al.
7,018,384 B2 3/2006 Skakoon
7,096,070 B1 8/2006 Jenkins et al.
7,206,641 B2 4/2007 Ignagni et al.
7,218,970 B2 5/2007 Ley et al.
7,239,918 B2 7/2007 Strother et al.
7,286,879 B2 10/2007 Wallace
7,317,948 B1 1/2008 King et al.
7,324,852 B2 1/2008 Barolat et al.
7,324,853 B2 1/2008 Ayal et al.
7,337,005 B2 2/2008 Kim et al.
7,337,006 B2 2/2008 Kim et al.
7,369,894 B2 5/2008 Gerber
7,389,149 B2 6/2008 Rossing et al.
7,444,181 B2 10/2008 Shi et al.
7,447,546 B2 11/2008 Kim et al.
7,450,993 B2 11/2008 Kim et al.
7,489,561 B2 2/2009 Armstrong et al.
7,493,175 B2 2/2009 Cates et al.
7,499,746 B2 3/2009 Buhlmann et al.
7,502,651 B2 3/2009 Kim et al.
7,515,971 B1 4/2009 Doan
7,553,313 B2 6/2009 Bagby
7,580,753 B2 8/2009 Kim et al.
7,668,598 B2 2/2010 Herregraven et al.
7,684,866 B2 3/2010 Fowler et al.
7,708,763 B2 5/2010 Selover et al.
7,761,166 B2 7/2010 Giftakis et al.
7,792,591 B2 9/2010 Rooney et al.
7,797,053 B2 9/2010 Atkinson et al.
7,813,803 B2 10/2010 Heruth et al.
7,908,015 B2 3/2011 Lazeroms et al.
7,917,230 B2 3/2011 Bly
7,930,039 B2 4/2011 Olson
7,981,144 B2 7/2011 Geist et al.
8,016,846 B2 9/2011 McFarlin et al.
8,065,020 B2 11/2011 Ley et al.
8,082,039 B2 12/2011 Kim et al.
8,170,690 B2 5/2012 Morgan et al.
8,229,565 B2 7/2012 Kim et al.
8,229,656 B2 7/2012 Ikushima et al.
8,249,701 B2 8/2012 Imran et al.
8,249,713 B2 8/2012 Fang et al.
8,295,945 B1 10/2012 Thacker et al.
8,321,021 B2 11/2012 Kisker et al.
8,380,318 B2 2/2013 Kishawi et al.
8,386,045 B2 2/2013 Zhao et al.
8,391,966 B2 3/2013 Luo et al.
8,409,233 B1 4/2013 Chinn et al.
8,428,728 B2 4/2013 Sachs
8,463,383 B2 6/2013 Sakai et al.
8,498,697 B2 7/2013 Yong et al.
8,606,358 B2 12/2013 Sachs
8,798,005 B1 8/2014 Vargantwar et al.
8,886,337 B2 11/2014 Bennett et al.
8,965,516 B2 2/2015 Bennett et al.
9,072,897 B2 7/2015 Sachs et al.
9,079,019 B2 7/2015 Crosby et al.
9,108,053 B2 8/2015 Crosby et al.
9,186,501 B2 11/2015 Rawat et al.
9,248,278 B2 2/2016 Crosby et al.
9,320,847 B2 4/2016 Rooney et al.
9,339,269 B2 5/2016 Geistert
9,474,906 B2 10/2016 Sachs et al.
9,561,364 B2 2/2017 Bondhus et al.
9,586,041 B2 3/2017 Goode et al.
9,649,490 B2 5/2017 Booker
9,861,811 B2 1/2018 Crosby et al.
9,889,294 B2 2/2018 Kalmann et al.
9,950,159 B2 4/2018 Beck et al.
9,981,122 B2 5/2018 Rawat et al.
9,999,763 B2 6/2018 Shiroff et al.
10,016,603 B2 7/2018 Sachs et al.
10,195,419 B2 2/2019 Shiroff et al.
10,327,810 B2 6/2019 Shiroff et al.
10,448,999 B2 10/2019 Schneider
10,449,355 B2 10/2019 Beck et al.
10,471,268 B2 11/2019 Crosby et al.

(56) References Cited

U.S. PATENT DOCUMENTS

| | | | |
|---|---|---|---|
| 10,653,440 | B2 | 5/2020 | Goode et al. |
| 10,661,078 | B2 | 5/2020 | Crosby et al. |
| 10,729,415 | B2 | 8/2020 | Roeder et al. |
| 10,828,490 | B2 | 11/2020 | Sachs et al. |
| 11,103,706 | B2 | 8/2021 | Sachs et al. |
| 11,331,488 | B2 | 5/2022 | Sachs et al. |
| 11,376,427 | B2 | 7/2022 | Beck et al. |
| 11,406,421 | B2 | 8/2022 | Shiroff et al. |
| 11,471,670 | B2 | 10/2022 | Crosby et al. |
| 11,679,261 | B2 | 6/2023 | Sachs et al. |
| 11,679,262 | B2 | 6/2023 | Sachs et al. |
| 11,684,774 | B2 | 6/2023 | Crosby |
| 11,937,847 | B2 | 3/2024 | Shiroff et al. |
| 11,951,310 | B2 | 4/2024 | Sachs et al. |
| 12,048,844 | B2 | 7/2024 | Crosby et al. |
| 12,121,728 | B2 | 10/2024 | Sachs et al. |
| 12,168,130 | B2 | 12/2024 | Sachs et al. |
| 12,285,612 | B1 | 4/2025 | Sachs et al. |
| 12,458,802 | B2 | 11/2025 | Sachs et al. |
| 12,582,816 | B2 | 3/2026 | Dahl et al. |
| 2001/0053885 | A1 | 12/2001 | Gielen et al. |
| 2002/0065543 | A1 | 5/2002 | Gomperz et al. |
| 2002/0068960 | A1 | 6/2002 | Saberski et al. |
| 2002/0099419 | A1 | 7/2002 | Cohen et al. |
| 2002/0115945 | A1 | 8/2002 | Herman et al. |
| 2002/0147485 | A1 | 10/2002 | Mamo et al. |
| 2002/0156513 | A1 | 10/2002 | Borkan |
| 2002/0161415 | A1 | 10/2002 | Cohen et al. |
| 2002/0183765 | A1 | 12/2002 | Adams |
| 2003/0100933 | A1 | 5/2003 | Ayal et al. |
| 2003/0120323 | A1 | 6/2003 | Meadows et al. |
| 2003/0120328 | A1 | 6/2003 | Jenkins et al. |
| 2003/0135120 | A1 | 7/2003 | Parks et al. |
| 2003/0199938 | A1 | 10/2003 | Smits et al. |
| 2003/0204228 | A1 | 10/2003 | Cross et al. |
| 2004/0030360 | A1 | 2/2004 | Eini et al. |
| 2004/0097986 | A1 | 5/2004 | Adams |
| 2004/0111118 | A1 | 6/2004 | Hill et al. |
| 2004/0122482 | A1 | 6/2004 | Tung et al. |
| 2004/0147969 | A1 | 7/2004 | Mann et al. |
| 2004/0167580 | A1 | 8/2004 | Mann et al. |
| 2004/0214790 | A1 | 10/2004 | Borgens |
| 2004/0230281 | A1 | 11/2004 | Heil et al. |
| 2004/0236383 | A1 | 11/2004 | Yelizarov |
| 2005/0070971 | A1 | 3/2005 | Fowler et al. |
| 2005/0075701 | A1 | 4/2005 | Shafer |
| 2005/0080472 | A1 | 4/2005 | Atkinson et al. |
| 2005/0107861 | A1 | 5/2005 | Harris et al. |
| 2005/0119713 | A1 | 6/2005 | Whitehurst et al. |
| 2005/0137644 | A1 | 6/2005 | Boveja et al. |
| 2005/0149154 | A1 | 7/2005 | Cohen et al. |
| 2005/0154389 | A1 | 7/2005 | Selover et al. |
| 2005/0165456 | A1 | 7/2005 | Mann et al. |
| 2005/0171551 | A1 | 8/2005 | Sukovich et al. |
| 2005/0177211 | A1 | 8/2005 | Leung et al. |
| 2005/0240243 | A1 | 10/2005 | Barolat et al. |
| 2005/0246006 | A1 | 11/2005 | Daniels |
| 2005/0283204 | A1 | 12/2005 | Buhlmann et al. |
| 2005/0288730 | A1 | 12/2005 | Deem et al. |
| 2006/0004429 | A1 | 1/2006 | Mrva et al. |
| 2006/0009810 | A1 | 1/2006 | Mann et al. |
| 2006/0009827 | A1 | 1/2006 | Kurth et al. |
| 2006/0032657 | A1 | 2/2006 | Zarembo |
| 2006/0041277 | A1 | 2/2006 | Deem et al. |
| 2006/0052856 | A1 | 3/2006 | Kim et al. |
| 2006/0074456 | A1 | 4/2006 | Pyles et al. |
| 2006/0106416 | A1 | 5/2006 | Raymond et al. |
| 2006/0111746 | A1 | 5/2006 | Foreman et al. |
| 2006/0111754 | A1 | 5/2006 | Rezai et al. |
| 2006/0155341 | A1 | 7/2006 | Tehrani et al. |
| 2006/0184222 | A1 | 8/2006 | Camps et al. |
| 2006/0206166 | A1 | 9/2006 | Weiner |
| 2006/0235484 | A1 | 10/2006 | Jaax et al. |
| 2006/0241716 | A1 | 10/2006 | Finch et al. |
| 2006/0259074 | A1 | 11/2006 | Kelleher et al. |
| 2006/0259099 | A1 | 11/2006 | Goetz et al. |
| 2006/0293662 | A1 | 12/2006 | Boyer et al. |
| 2007/0027501 | A1 | 2/2007 | Jensen et al. |
| 2007/0049980 | A1 | 3/2007 | Zielinski et al. |
| 2007/0060967 | A1 | 3/2007 | Strother et al. |
| 2007/0073357 | A1 | 3/2007 | Rooney et al. |
| 2007/0100377 | A1 | 5/2007 | Armstrong et al. |
| 2007/0100391 | A1 | 5/2007 | Armstrong |
| 2007/0100408 | A1 | 5/2007 | Gerber |
| 2007/0100411 | A1 | 5/2007 | Bonde |
| 2007/0123954 | A1 | 5/2007 | Gielen et al. |
| 2007/0129780 | A1 | 6/2007 | Whitehurst et al. |
| 2007/0135768 | A1 | 6/2007 | Carlsen |
| 2007/0179557 | A1 | 8/2007 | Maschino et al. |
| 2007/0208392 | A1 | 9/2007 | Kuschner et al. |
| 2007/0232936 | A1 | 10/2007 | Mann et al. |
| 2007/0239224 | A1 | 10/2007 | Bennett et al. |
| 2007/0276453 | A1 | 11/2007 | Hill et al. |
| 2008/0026981 | A1 | 1/2008 | Muhrer et al. |
| 2008/0027505 | A1 | 1/2008 | Levin et al. |
| 2008/0103570 | A1 | 5/2008 | Gerber |
| 2008/0103573 | A1 | 5/2008 | Gerber |
| 2008/0103574 | A1 | 5/2008 | Gerber |
| 2008/0103579 | A1 | 5/2008 | Gerber |
| 2008/0132961 | A1 | 6/2008 | Jaax et al. |
| 2008/0132969 | A1 | 6/2008 | Bennett et al. |
| 2008/0147156 | A1 | 6/2008 | Imran |
| 2008/0167698 | A1 | 7/2008 | Kim et al. |
| 2008/0177351 | A1 | 7/2008 | Fang et al. |
| 2008/0183221 | A1 | 7/2008 | Burdulis |
| 2008/0183257 | A1 | 7/2008 | Imran et al. |
| 2008/0200972 | A1 | 8/2008 | Rittman et al. |
| 2008/0228241 | A1 | 9/2008 | Sachs |
| 2008/0234791 | A1 | 9/2008 | Arle et al. |
| 2008/0269716 | A1 | 10/2008 | Bonde et al. |
| 2008/0269812 | A1 | 10/2008 | Gerber et al. |
| 2009/0005833 | A1 | 1/2009 | Cameron et al. |
| 2009/0018576 | A1 | 1/2009 | Binmoeller |
| 2009/0020764 | A1 | 1/2009 | Anderson et al. |
| 2009/0105700 | A1 | 4/2009 | Anderson |
| 2009/0112263 | A1 | 4/2009 | Pool et al. |
| 2009/0192567 | A1 | 7/2009 | Armstrong et al. |
| 2009/0210041 | A1 | 8/2009 | Kim et al. |
| 2009/0248095 | A1 | 10/2009 | Schleicher et al. |
| 2009/0254095 | A1 | 10/2009 | Levine et al. |
| 2009/0259280 | A1 | 10/2009 | Wilkin et al. |
| 2009/0299201 | A1 | 12/2009 | Gunderson |
| 2009/0299444 | A1 | 12/2009 | Boling |
| 2009/0326613 | A1 | 12/2009 | Knoblich |
| 2010/0010585 | A1 | 1/2010 | Davis et al. |
| 2010/0030227 | A1 | 2/2010 | Kast et al. |
| 2010/0036280 | A1 | 2/2010 | Ballegaard et al. |
| 2010/0036454 | A1 | 2/2010 | Bennett et al. |
| 2010/0082086 | A1 | 4/2010 | Zhu |
| 2010/0114206 | A1 | 5/2010 | Kaemmerer et al. |
| 2010/0137938 | A1 | 6/2010 | Kishawi et al. |
| 2010/0152808 | A1 | 6/2010 | Boggs, II |
| 2010/0152809 | A1 | 6/2010 | Boggs, II |
| 2010/0174240 | A1 | 7/2010 | Wells et al. |
| 2010/0174326 | A1 | 7/2010 | Selover et al. |
| 2010/0179562 | A1 | 7/2010 | Linker et al. |
| 2010/0185161 | A1 | 7/2010 | Pellegrino et al. |
| 2010/0211149 | A1 | 8/2010 | Morgan et al. |
| 2010/0249875 | A1 | 9/2010 | Kishawi et al. |
| 2010/0280576 | A1 | 11/2010 | Gerber et al. |
| 2010/0292769 | A1 | 11/2010 | Brounstein et al. |
| 2010/0331883 | A1 | 12/2010 | Schmitz et al. |
| 2011/0004269 | A1 | 1/2011 | Strother et al. |
| 2011/0021943 | A1 | 1/2011 | Lacour et al. |
| 2011/0022114 | A1 | 1/2011 | Navarro |
| 2011/0022123 | A1 | 1/2011 | Stancer et al. |
| 2011/0054565 | A1 | 3/2011 | Wacnik et al. |
| 2011/0106207 | A1 | 5/2011 | Cauller et al. |
| 2011/0160538 | A1 | 6/2011 | Ravikumar et al. |
| 2011/0190786 | A1 | 8/2011 | Gerber et al. |
| 2011/0202112 | A1 | 8/2011 | Ruais |
| 2011/0224665 | A1 | 9/2011 | Crosby et al. |
| 2011/0224682 | A1 | 9/2011 | Westlund et al. |
| 2011/0251662 | A1 | 10/2011 | Griswold et al. |

(56) References Cited

U.S. PATENT DOCUMENTS

| | | | |
|---|---|---|---|
| 2011/0257660 | A1 | 10/2011 | Jones et al. |
| 2011/0270340 | A1 | 11/2011 | Pellegrini et al. |
| 2012/0035953 | A1 | 2/2012 | Armstrong |
| 2012/0089153 | A1 | 4/2012 | Christopherson et al. |
| 2012/0116477 | A1 | 5/2012 | Crowe et al. |
| 2012/0192874 | A1 | 8/2012 | Bolea et al. |
| 2012/0209285 | A1 | 8/2012 | Barker et al. |
| 2012/0215218 | A1 | 8/2012 | Lipani |
| 2012/0283800 | A1 | 11/2012 | Perryman et al. |
| 2012/0290055 | A1 | 11/2012 | Boggs, II |
| 2012/0310140 | A1 | 12/2012 | Kramer et al. |
| 2012/0310301 | A1 | 12/2012 | Bennett et al. |
| 2012/0310302 | A1 | 12/2012 | Bennett et al. |
| 2012/0310314 | A1 | 12/2012 | Bennett et al. |
| 2012/0323253 | A1 | 12/2012 | Garai et al. |
| 2013/0023974 | A1 | 1/2013 | Amrani |
| 2013/0053926 | A1 | 2/2013 | Hincapie Ordonez et al. |
| 2013/0096641 | A1 | 4/2013 | Strother et al. |
| 2013/0105071 | A1* | 5/2013 | DiGiore .................. A61N 1/05 29/857 |
| 2013/0106347 | A1 | 5/2013 | Kallmyer et al. |
| 2013/0131766 | A1 | 5/2013 | Crosby et al. |
| 2013/0155117 | A1 | 6/2013 | Bang |
| 2013/0197607 | A1 | 8/2013 | Wilder et al. |
| 2013/0197615 | A1 | 8/2013 | Rundle et al. |
| 2013/0211487 | A1 | 8/2013 | Fang et al. |
| 2013/0218247 | A1 | 8/2013 | Sachs |
| 2013/0238066 | A1 | 9/2013 | Boggs, II et al. |
| 2013/0245715 | A1 | 9/2013 | Peterson |
| 2013/0253605 | A1 | 9/2013 | Bennett et al. |
| 2013/0261696 | A1 | 10/2013 | Thacker et al. |
| 2013/0296966 | A1 | 11/2013 | Wongsarnpigoon et al. |
| 2013/0310901 | A1 | 11/2013 | Perryman et al. |
| 2013/0338730 | A1 | 12/2013 | Shiroff et al. |
| 2014/0029695 | A1 | 1/2014 | Liu et al. |
| 2014/0031837 | A1 | 1/2014 | Perryman et al. |
| 2014/0039574 | A1 | 2/2014 | Bradley |
| 2014/0046398 | A1 | 2/2014 | Sachs et al. |
| 2014/0058476 | A1 | 2/2014 | Crosby et al. |
| 2014/0114385 | A1 | 4/2014 | Nijhuis et al. |
| 2014/0277022 | A1 | 9/2014 | Perrin et al. |
| 2014/0288616 | A1 | 9/2014 | Rawat et al. |
| 2014/0350653 | A1* | 11/2014 | Shiroff .................... A61N 1/05 607/116 |
| 2015/0101188 | A1 | 4/2015 | Klardie et al. |
| 2015/0105840 | A1 | 4/2015 | Boggs, II |
| 2015/0306405 | A1 | 10/2015 | Sachs et al. |
| 2015/0374992 | A1 | 12/2015 | Crosby et al. |
| 2016/0045746 | A1 | 2/2016 | Jiang et al. |
| 2016/0045747 | A1 | 2/2016 | Jiang et al. |
| 2016/0067476 | A1 | 3/2016 | Rawat et al. |
| 2016/0106994 | A1 | 4/2016 | Crosby et al. |
| 2016/0213927 | A1 | 7/2016 | McGee et al. |
| 2016/0310732 | A1 | 10/2016 | Beck et al. |
| 2017/0100408 | A1 | 4/2017 | Bertolini et al. |
| 2017/0312500 | A1* | 11/2017 | Shoberg ............... A61N 1/0551 |
| 2018/0008311 | A1 | 1/2018 | Shiroff et al. |
| 2018/0133461 | A1 | 5/2018 | Crosby et al. |
| 2018/0256906 | A1 | 9/2018 | Pivonka et al. |
| 2018/0353757 | A1 | 12/2018 | Sachs et al. |
| 2019/0167995 | A1 | 6/2019 | Sachs et al. |
| 2019/0328423 | A1 | 10/2019 | Shiroff et al. |
| 2020/0203858 | A1 | 6/2020 | Youtsey |
| 2025/0249252 | A1 | 8/2025 | Sachs et al. |

FOREIGN PATENT DOCUMENTS

| | | | |
|---|---|---|---|
| CN | 101678203 | A | 3/2010 |
| EP | 0587269 | A2 | 3/1994 |
| EP | 0587269 | B1 | 12/1998 |
| EP | 1053762 | A2 | 11/2000 |
| EP | 1255583 | A1 | 11/2002 |
| EP | 1053762 | B1 | 8/2005 |
| EP | 1255583 | B1 | 12/2007 |
| EP | 2125100 | A1 | 12/2009 |
| EP | 2273931 | A2 | 1/2011 |
| WO | WO-0158520 | A1 | 8/2001 |
| WO | WO-2004066820 | A2 | 8/2004 |
| WO | WO-2006091611 | A1 | 8/2006 |
| WO | WO-2006133445 | A2 | 12/2006 |
| WO | WO-2006135791 | A2 | 12/2006 |
| WO | WO-2007047954 | A2 | 4/2007 |
| WO | WO-2007051146 | A1 | 5/2007 |
| WO | WO-2007138598 | A2 | 12/2007 |
| WO | WO-2008048471 | A2 | 4/2008 |
| WO | WO-2008070807 | A2 | 6/2008 |
| WO | WO-2008094952 | A2 | 8/2008 |
| WO | WO-2008112178 | A1 | 9/2008 |
| WO | WO-2009020764 | A1 | 2/2009 |
| WO | WO-2009134475 | A1 | 11/2009 |
| WO | WO-2010062600 | A1 | 6/2010 |
| WO | WO-2010062622 | A2 | 6/2010 |
| WO | WO-2011079866 | A1 | 7/2011 |
| WO | WO-2011112773 | A2 | 9/2011 |
| WO | WO-2012057916 | A1 | 5/2012 |
| WO | WO-2012091747 | A1 | 7/2012 |
| WO | WO-2013016268 | A1 | 1/2013 |
| WO | WO-2013019853 | A1 | 2/2013 |
| WO | WO-2013036630 | A1 | 3/2013 |
| WO | WO-2013096260 | A1 | 6/2013 |
| WO | WO-2013138786 | A1 | 9/2013 |
| WO | WO-2013155117 | A1 | 10/2013 |
| WO | WO-2014099423 | A1 | 6/2014 |
| WO | WO-2015059570 | A1 | 4/2015 |
| WO | WO-2015187426 | A1 | 12/2015 |
| WO | WO-2017044904 | A1 | 3/2017 |
| WO | WO-2017062508 | A1 | 4/2017 |
| WO | WO-2018007914 | A1 | 1/2018 |

OTHER PUBLICATIONS

Baker, et al., Clinical Uses of Neuromuscular Electrical Stimulation, NeuroMuscular Electrical Stimulation—A Practical Guide, 4th ed., Rancho Los Amigos Research and Education Institute Inc (pp. 47-66) (2000).

Bhadra, et al., Peripheral nerve stimulation for restoration of motor function, Journal of Clinical Neurophysiology: Official Publication of the American Electroencephalographic Society, 14(5):378-33 (Sep. 1997).

Bogie, et al., Effects of Regular Use of Neuromuscular Electrical Stimulation on Tissue Health, Journal of Rehabilitation Research and Development, 40(6):469-475 (2003) available at: http://www.ncbi.nlm.nih.gov/pubmed/15077659 (Accessed Jan. 18, 2011).

Bowman, et al., Effects of Waveform Parameters on Comfort during Transcutaneous Neuromuscular Electrical Stimulation, Annals of Biomedical Engineering, 13:59-74 (1985).

Bradford, et al., Surface Electrical Stimulation in the Treatment of Idiopathic Scoliosis: Preliminary Results in 30 Patients, Spine, 8(7):757-764 (1983).

Brazier, et al., A Comparison of the EQ-5D and SF-6D Across Seven Patient Groups, Health Economics, 13:873-884 (2004).

Chou et al., "Interventional Therapies, Surgery, and Interdisciplinary Rehabilitation for Low Back Pain: An Evidence-Based Clinical Practice Guideline From the American Pain Society." Spine, 34(10):1066-1077 (2009).

Coghlan, et al., Electrical Muscle Stimulation for Deep Stabilizing Muscles in Abdominal Wall, Conference proceedings: Annual International Conference of the IEEE Engineering in Medicine and Biology Society, IEEE Engineering in Medicine and Biology Society, Conference, 2008 (pp. 2756-2759)available at: http://www.ncbi.nlm.nih.gov/pubmed/19163276.

Coghlan, et al., Neuromuscular Electrical Stimulation Training Results in Enhanced Activation of Spinal Stabilizing Muscles During Spinal Loading and Improvements in Pain Ratings, Conference proceedings: Annual International Conference of the IEEE Engineering in Medicine and Biology Society, IEEE Engineering in Medicine and Biology Society, Conference, 2011 (pp. 7622-7625) available at: http://www.ncbi.n1m.nih.gov/pubmed/22256103.

(56) References Cited

OTHER PUBLICATIONS

Costa et al., Motor Control Exercise for Chronic Low Back Pain: A Randomized Placebo-Controlled Trial, Physical Therapy, 89(12):1275-1286 (2009).
Crago, et al., The Choice of Pulse Duration for Chronic Electrical Stimulation via Surface, Nerve, and Intramuscular Electrodes, Annals of Biomedical Engineering, 2(3):252-264 (1974).
Criterion Inc., NMES Treatment Protocols, 3 pages (accessed Jun. 7, 2012) available at http://www.criterionmed.com/PDF/NMES%20Treatment%20Protocols.pdf.
Deckers, et al., Chronic Low Back Pain: Restoration of Dynamic Stability, Neuromodulation, 18:478-486 (2015).
Durham, et al., Surface Electrical Stimulation Versus Brace in Treatment of Idiopathic Scoliosis, Spine, 15(9):888-891 (1990).
Dworkin et al., Interpreting the Clinical Importance of Treatment Outcomes in Chronic Pain Clinical Trials: IMMPACT Recommendations, The Journal of Pain, 9(2):105-121 (2008).
Eldabe et al., "Complications of Spinal Cord Stimulation and Peripheral Nerve Stimulation Techniques: A Review of the Literature." Pain Medicine, 17:325-336 (2016).
EMPI, Low Back Syndrome/Chronic Low Back Pain, NMES Guidelines for Treatment, 2 pages (2003).
Extended European Search Report dated Jan. 7, 2013 in EP Patent Appl. Serial No. 12176863.
Extended European Search Report dated Feb. 24, 2020 in EP Patent Appl. Serial No. 08726632.6.
Extended European Search Report dated Mar. 5, 2015 in EP Patent Appl. Serial No. 14189412.1.
Extended European Search Report dated Sep. 30, 2019 in EP Patent Appl. Serial No. 19173003.5.
Farrar et al., "Use of the Cumulative Proportion of Responders Analysis Graph to Present Pain Data Over Range of Cut-Off Points: Making Clinical Trial Data More Understandable." J Pain Symptom Manage, 31(4):369-377 (2006).
Federov et al., "Consequences of dichotomization." Pharmaceut. Statist., 8:50-61 (2009).
Ferreira, et al., Comparison of general exercise, motor control exercise and spinal manipulative therapy for chronic low back pain: A randomized trial, Pain, 131(1-2):31-37 (2007) available at: http://www.ncbi.nlm.nih.gov/pubmed/17250965.
Follett, et al., Prevention and Management of Intrathecal Drug Delivery and Spinal Cord Stimulation System Infections, Anesthesiology, 100:1582-94 (2004).
Freeman, et al., The Role of the Lumbar Multifidus in Chronic Low Back Pain: A Review, American Academy of Physical Medicine and Rehabilitation, 2:142-146 (2010).
Friedman, et al., Electrical stimulation for scoliosis, American Family Physician, 25(4):155-160 (1982) available at: http://www.ncbi.n1m.nih.gov/pubmed/6978055 (Accessed Oct. 19, 2011).
Garmirian , et al., Discriminating Neurogenic from Myopathic Disease via Measurement of Muscle Anisotrophy, Muscle Nerve, 39(1):16-24 (2009) (abstract).
Gazelle, et al., Tumor Ablation with Radio-frequency Energy, Radiology, 217(3):633-646 (2000).
Ghamkhar, et al., *Application of rehabilitative ultrasound in the assessment of low back pain: a literature review*, Journal of Bodywork & Movement Therapies, 15(4):465-477 (2011).
Gilmore, et al., A Review of Peripheral Nerve Stimulation Techniques Targeting the Medial Branches of the Lumbar Dorsal Rami in the Treatment of Chronic Low Back Pain, Pain Medicine, 21(S1):S41-S46 (2020).
Glaser, et al., Electrical Muscle Stimulation as an Adjunct to Exercise Therapy in the Treatment of Nonacute Low Back Pain: A Randomized Trial, The Journal of Pain, 2(5), pp. 295-300 (2001).
Gondin, et al., "Electromyostimulation Training Effects on Neural Drive and Muscle Architecture." Med. Sci. Sports Exerc., 37(8):1291-1299, (2005).
Gondin, et al., Electromyostimulation Training Effects on Neural Drive and Muscle Architecture, Medicine & Science in Sports & Exercise, 37(8):1291-1299 (Aug. 2005).
Gorman, et al., The Effect of Stimulus Parameters on the Recruitment Characteristics of Direct Nerve Stimulation, IEEE Transactions on Bio-medical Engineering, 30 (7): 407-414 (1983).
Haemmerich, et al., Thermal Tumour Ablation: Devices, Clinical Applications and Future Directions, Int. J. Hyperthermia, 21(8):755-760 (2005) (abstract).
Hagg, et al., The Clinical Importance of Changes in Outcome Scores After Treatment for Chronic Low Back Pain, Eur. Spine. J., 12:12-20 (2003).
Hauggaard et al., "Specific spinal stabilisation exercises in patients with low back pain—a systematic review." Physical Therapy Reviews, 12(3):233-248 (2007).
Hayek et al., "Treatment-Limiting Complications of Percutaneous Spinal Cord Stimulator Implants: A Review of Eight Years of Experience from an Academic Center Database." Neuromodulation, 18:603-609 (2015).
Hebert et al., *The Relationship of Transversus Abdominis and Lumbar Multifidus Activation and Prognostic Factors for Clinical Success With a Stabilization Exercise Program: A Cross-Sectional Study*, Arch. Phys. Med. Rehabil., 91:78-85 (2010).
Herbert, et al., Scoliosis Treatment in Children Using a Programmable, Totally Implantable Muscle Stimulator (ESI), IEEE Transactions on Biomedical Engineering, 36(7): 801-802(Jul. 1989).
Hides et al., Long-Term Effects of Specific Stabilizing Exercises for First-Episode Low Back Pain, *Spine*, 26(11):E243-248 (2001).
Hodges, et al., Intervertebral Stiffness of the Spine is Increased by Evoked Contraction of Transversus Abdominis and the Diaphragm: in Vivo Porcine Studies, Spine 28(23):2594-2601 (Dec. 1, 2003) (abstract).
Hodges, et al., Response of the Deep Paraspinal Muscles to Cortical but not Transmastoid Stimulation is Increased at a Single Lumbar Level Following Interverebral Disc Lesion, Progress in Motor Control Vi—Brazil., 36:2-3 (2007).
Hodges., Is there a Role for Transversus Abdominis in Lumbo-Pelvis Stability?, Manual Therapy, 4(2):74-86, (1999).
Holm, et al, Sensorimotor Control of the Spine, J. Electromyogr. Kinesiol., 12(3):219-234 (2002), (Abstract).
Hortobagyi, et al., Neural adaptations to Electrical Stimulation Strength Training, European Journal of Applied Physiology, 2011 (pp. 2439-2449) available at: http://www.ncbi.nlm.nih.gov/pubmed/21643920 (Accessed Jul. 19, 2011).
Informal Response to Written Opinion dated Jan. 17, 2012 in Int'l PCT Patent Appl. Serial No. PCT/US2011/027834.
International Search Report & Written Opinion dated Apr. 5, 2013 in Int'l PCT Patent Application Serial No. PCT/US2012/070259.
International Search Report & Written Opinion dated Jan. 19, 2016 in Int'l PCT Patent Appl. Serial No. PCT/IB2015/055926.
International Search Report & Written Opinion dated Jun. 25, 2008 in Int'l PCT Patent Appl. No. PCT/US08/03126.
International Search Report & Written Opinion dated Oct. 20, 2017 in Int'l PCT Patent Appl. Serial No. PCT/IB2017/053946.
International Search Report & Written Opinion dated Sep. 28, 2017 in Int'l PCT Patent Appl. Serial No. PCT/IB2017/053945.
International Search Report & Written Opinion dated Mar. 19, 2015 in Int'l PCT Patent Appl. Serial No. PCT/IB2014/002920.
International Search Report & Written Opinion dated Sep. 3, 2013 in Int'l PCT Application No. PCT/US2013/045223.
International Search Report & Written Opinion dated Oct. 17, 2012 in Int'l PCT Patent Appl. No. PCT/US12/49148.
International Search Report & Written Opinion dated Oct. 19, 2011 in Int'l PCT Patent Appl. No. PCT/US11/27834, 12 pages.
International Search Report and Written Opinion dated Jan. 26, 2016 in Int'l PCT Patent Appl. Serial No. PCT/IB2015/057838.
International Search Report and Written Opinion dated Oct. 16, 2015 in Int'l PCT Patent Appl. Serial No. PCT/US2015/032732.
International Search Report dated Oct. 19, 2011 in Int'l PCT Patent Appl No. PCT/US2011/027934, 5 pages.
Jinkins, Randy, The Anatomic and Physiologic Basis of Local, Referred and Radiating Lumbosacral Pain Syndromes Related to Disease of the Spine, J. Neuroradiol., 31:163-80 (2004).
Keller, et al., Muscular Contributions to Dynamic Dorsoventral Lumber Spine Stiffness, Eur. Spine J. 16(2): 245-254 (Apr. 29, 2006).

(56) References Cited

OTHER PUBLICATIONS

Kiesel, et al., Measurement of Lumbar Multifidus Muscle Contraction with Rehabilitative Ultrasound Imaging, Manual Therapy, 12(2):161-166 (2007) available at: http://www.ncbi.nlm.nih.gov/pubmed/16973400.
Lauridsen, et al., Responsiveness and Minimal Clinically Important Difference for Pain and Disability Instruments in Low Back Pain Patients, BMC Musculoskeletal Disorders, 7(82):16 pages (2006).
Lieber, Richard., Comparison between Animal and Human Studies of Skeletal Muscle Adaptation to Chronic Stimulation, Clinical Orthopaedics and Related Research, 233:19-24 (1988).
Lieber, Richard L., Skeletal Muscle Adaptability. II: Muscle Properties Following Spinal-Cord Injury, Developmental Medicine and Child Neurology, 28(4):533-542 (Aug. 1986).
Lieber, Richard L., Skeletal Muscle Adaptability. III: Muscle Properties Following Chronic Electrical Stimulation, Developmental medicine and child neurology, 28(5):662-670 (Oct. 1986).
Mcintosh, et al., Low back pain (chronic), Clin. Evid., 10:1-28(2008).
Medtronic Extension Passer 3555 Accessory Kit—Technical Instructions, 2 pages (2001).
Medtronic Interstim Therapy 3093 & 3889—Implant Manual, 38 pages (2010).
Medtronic, Kinetra, Soletra, and Itrel II, 8870, Neurostimulators for Deep Brain Stimulation (DBS), Software Application Card, Programming Guide for Software A, Dec. 1, 2003, Published 2005, Retrieved from the Internet: URL: http::/www.boala-parkinson.ro/Carti%20tehnice/dbs-prog8870-gd.pdf [retrieved Aug. 23, 2018].
Medtronic Model 3464 Receiver/Extension Internalization Manual, SE-4 for Spinal Cord Stimulation (SCS), 7 pages (1986).
Medtronic Tunneling Rod Accessory Kit 8590-41—Technical Manual, 9 pages (No date available).
MicroProbes for Life Science, Nerve Cuff electrodes,2018, available at https://microprobes.com/products/peripheral-electrodes/nerve-cuff, accessed Mar. 5, 2018.
Miyatani, et al., Validity of Estimating Limb Muscle Volume by Bioelectrical Impedance, J. Appl. Physiol., 91:386-394, (2001).
Mortimer, et al., Intramuscular electrical stimulation: tissue damage, Annals of Biomedical Engineering, 8(3):235-244 (1980).
Mortimer, et al., Peripheral Nerve and Muscle Stimulation. In: Horch KW, Dhillon G, eds, Neuroprosthetics: Theory and Practice (Series on Bioengineering & Biomedical Engineering—vol. (2), 2005, World Scientific Publishing Company, (pp. 1-48).
Nachemson, et al., Effectiveness of Treatment with a Brace in Girls Who Have Adolescent Idiopathic Scoliosis, The Journal of Bone and Joint Surgery, 77-A(6):815-822 (Jun. 1995).
OAAO Bock, ActiGait Implantable Drop Foot Stimulator, Surgeon Manual, 2006 (28 pages).
O'Donnell, et al., Electrical Stimulation in the Treatment of Idiopathic Scoliosis, Clinical Orthopaedics and Related Research, No. 229:107-112 (Apr. 1988).
Ostelo et al., Interpreting Change Scores for Pain and Functional Status in Low Back Pain: Towards International Consensus Regarding Minimal Important Change, Spine, 33(1):90-94 (2008).
Paicius, et al., Peripheral Nerve Field Stimulation for the Treatment of Chronic Low Back Pain: Preliminary Results of Long-Term Follow-up: A Case Series, Neuromodulation, 10(3):279-290 (2007) available at: http://www.blackwell-synergy.com/doi/abs/10.llll/j.1525-1403.2007.00116.x.
Panjabi, Manohar., A hypothesis of Chronic Back Pain: Ligament Sub-Failure Injuries Lead to Muscle Control Dysfunction, European spine journal: official publication of the European Spine Society, the European Spinal Deformity Society, and the European Section of the Cervical Spine Research Society 15(5): 668-676, (May 2006), http://www.ncbi.nlm.nih.gov/pubmed/16047209.
Panjabi, Manohar., The Stabilizing System of the Spine, Part 1, Function, Dysfunction, Adaptation, and Enhancement, Journal of Spinal Disorders, 5(4)383-389 (Dec. 1992), Discussion 397., http://www.ncbi.nlm.nih.gov/pubmed/1490034.
Panjabi, Manohar., The stabilizing system of the spine, Part II, Neutral zone and instability hypothesis, Journal of Spinal Disorders, 5(4):390-396 (Dec. 1992), Discussion 397. http://www.ncbi.nlm.nih.gov/pubmed/1490035.
Partial International Search Report dated Aug. 4, 2015 in Int'l PCT Patent Application Serial No. PCT/US2015/032732.
PCT Written Opinion dated Aug. 23, 2013 in Int'l PCT Patent Appl. Serial No. PCT/US2010/049148.
Peckham, et al., Functional Electrical Stimulation for Neuromuscular Applications, Annual review of Biomedical Engineering, 7:327-360 (2005) available at: http://www.ncbi.nlm.nih.gov/pubmed/16004574.
Peterson, et al., Long-term Intramuscular Electrical Activation of the Phrenic Nerve: Safety and Reliability, IEEE Transactions on Bio-medical Engineering, 41(12):1115-1126 (1994).
Poitras, et al., Evidence-informed Management of Chronic Low Back Pain with Transcutaneous Electrical Nerve Stimulation, Interferential Current, Electrical Muscle Stimulation, Ultrasound, and Thermotherapy, The Spine Journal, 8:226-233 (2008).
Reed B., The Physiology of Neuromuscular Electrical Stimulation, Pediatric Physical Therapy, 9(3):96-102 (1997) available at: http://journals.lww.com/pedpt/pages/articleviewer.aspx?year=1997&issue=00-930&article=00002&type=abstract.
Rosatelli, et al., Three-Dimensional Study of the Musculotendinous Architecture of Lumber Multifidus and its Functional Implications, Clinical Anatomy, 21(6):539-544 (Sep. 2008).
RS Medical, RS-4M Muscle Stimulator, available at http://www.rsmedical.com/documents/fact_sheet_RS4m.pdf (last visited Jul. 19, 2012).
Russo, et al., Muscle Control and Non-specific Chronic Low Back Pain, Neuromodulation: Technology at the Neural Interface, 21:1-9 (2017).
Rutkove., Electrical Impedance Myography: Background, Current State, and Future Directions, Muscle Nerve, 40(6):936-946 (2009).
Schwartz, et al., Therapeutic Electrical Stimulation of the Hypoglossal Nerve in Obstructive Sleep Apnea, Arch Otolaryngal Head Neck Surg., 127:1216-1223 (2001).
Senn et al., "Measurement in clinical trials: A neglected issue for statisticians?" Statist. Med., 28:3189-3209 (2009).
Sheffler et al., Neuromuscular Electrical Stimulation in Neurorehabilitation, Muscle Nerve, 35:562-590 (2007).
Sippl, Charles J., Computer Dictionary: Third Edition, pp. 2257 and 2340 (1984).
Sluijter, Radiofrequency Ablation in the Management of Spinal Pain, C212, IV(1):10-15, (2006).
Soer et al., *Clinimetric properties of the EuroQol-50 in patients with chronic low backpain*, The Spine Journal, 12:1035-1039 (2012).
Solomonow, et al., The Ligamento-Muscular Stabilizing System of the Spine, Spine, 23(23):2552-2562, (1998).
Spinal Fusion Guidelines, MD Guidelines, 2009. www.mdguidelines.com/spinal-fusion.
Stokes, et al., Surface EMG Electrodes Do Not Accurately Record from Lumbar Multifidus Muscles, Clin. Biomech, 18(1):9-13, (2003), (Abstract Only).
Unit III—The Spine, "Motions of the Spine," available at https://courses.vcu.edu/DANC291-003/unit_3.htm, accessed Mar. 5, 2018.
Van Buyten et al., *Neuromuscular Reactivation- A New Therapy for Patients with Chronic Low Back Pain* (*CLBP*): *Results of a European Multicenter Feasibility Study*, Neuromodulation, 16:e176 (2013).
Van Dieen, et al., Trunk Muscle Recruitment Patterns in Patients with Low Back Pain Enhance the Stability of the Lumbar Spine, Spine, (2003), 28(8):834-841 (Abstract Only).
Van, et al., The Use of Real-Time Ultrasound Imaging for Biofeedback of Lumbar Multifidus Muscle Contraction in Healthy Subjects, The Journal of Orthopaedic and Sports Physical Therapy, 36(12):920-925 (2006) available at: http://www.ncbi.n1m.nih.gov/pubmed/17193869.
Verrills, et al., Peripheral Nerve Stimulation: A Treatment for Chronic Low Back Pain and Failed Back Surgery Syndrome?, Neuromodulation: Technology at the Neural Interface, 12(1):68-75, (2009).
Vrbova et al., Application of Muscle/Nerve Stimulation in Health and Disease, Springer Verlag (2008) available at: http://books.google.

(56) References Cited

OTHER PUBLICATIONS com/books?h1=en&1r=&id=jb8fDGxkbqEC&oi=fn-d&pg=PA1&dq=Application+of+Muscle/Nerve+Stimulation+in+Health+and+-Disease&ots=CMV5rXiDQD&sig=Wg8ulYOC4PgvVDzcjdwBub5U2To (Accessed Jun. 2, 2011).
Wallwork, et al., The Effect of Chronic Low Back Pain on Size and Contraction of the Lumbar Multifidus Muscle, Manual Therapy, 14(5):496-500 (2009) available at: http://www.ncbi.nlm.nih.gov/pubmed/19027343.
Ward, et al., Architectural Analysis and Intraoperative Measurements Demonstrate the Unique Design of the Multifidus for Lumbar Spine Stability, J. Bone Joint Surg. [Am.] 91:176-185, PMC2663324 (2009).
Wright et al., Morphologic and Histochemical Characteristics of Skeletal Muscle after Long-Term Intramuscular Electrical Stimulation, Spine, 17(7):767-770 (1992) available at: http://www.ncbi.nlm.nih.gov/pubmed/1502640 (Accessed Aug. 2, 2011).
Written Opinion dated Nov. 16, 2011 in Int'l PCT Patent Appl. No. PCT/US2011/027934, 7 pages.
Written Opinion of the International Preliminary Examining Authority dated Feb. 3, 2014 in Int'l PCT Patent Appl. Serial No. PCT/US2012/070259.
Zundert, et al., Radiofrequency Treatment for Chronic Pain Syndromes, CPD Anaesthesia, 6(1):13-17 (2004).
"Ineffective treatments for low back pain might actually make the pain (and treatment worse," The Mighty, Military News, https://www.wearethemight.com/sponsored-content/ineffective-treatments-for-low-back-pain-might-actually-make-the-pain-and-treatment-worse/, accessed Oct. 10, 2023.
Jensen, et al., Mechanisms of spinal cord stimulation for the treatment of pain: Still in the dark after 50 years, Eur. J. Pain, 23:652-659 (2019).
"Mainstay Medical Announces Positive Outcomes From Landmark Restore Clinical Trial of ReActiv8 (R)," Businesswire.com (Jan. 15, 2025).
Schwab, et al., Restorative Neurostimulation Therapy Compared to Optimal Medical Management: A Randomized Evaluation (Restore) for the Treatment of Chronic Mechanical Low Back Pain due to Multifidus Dysfunction, Pain. Ther. 24:401-423 (2025).
U.S. Appl. No. 12/075,174 / U.S. Pat. No. 8,428,728, filed Mar. 10, 2008 / Apr. 23, 2013.
U.S. Appl. No. 13/045,421 / U.S. Pat. No. 9,248,278, filed Mar. 10, 2011 / Feb. 2, 2016.
U.S. Appl. No. 13/045,435 / U.S. Pat. No. 10,925,637, filed Mar. 10, 2011 / Feb. 3, 2021.
U.S. Appl. No. 13/564,584 / U.S. Pat. No. 9,079,019, filed Aug. 1, 2012 / Jul. 14, 2015.
U.S. Appl. No. 13/718,806 / U.S. Pat. No. 9,108,053, filed Dec. 18, 2012 / Aug. 18, 2015.
U.S. Appl. No. 13/797,100 / U.S. Pat. No. 9,999,763, filed Mar. 12, 2013 / Jun. 19, 2018.
U.S. Appl. No. 13/858,809 / U.S. Pat. No. 8,606,358, filed Apr. 8, 2013 / Dec. 10, 2013.
U.S. Appl. No. 14/061,614 / U.S. Pat. No. 9,072,897, filed Oct. 23, 2013 / Jul. 7, 2015.
U.S. Appl. No. 14/295,153 / U.S. Pat. No. 9,186,501, filed Jun. 3, 2014 / Nov. 17, 2015.
U.S. Appl. No. 14/453,423 / U.S. Pat. No. 10,195,419, filed Aug. 6, 2014 / Feb. 5, 2019.
U.S. Appl. No. 14/792,430 / U.S. Pat. No. 9,474,906, filed Jul. 6, 2015 / Oct. 25, 2016.
U.S. Appl. No. 14/849,478 / U.S. Pat. No. 9,861,811, filed Sep. 9, 2015 / Jan. 9, 2018.
U.S. Appl. No. 14/882,087 / U.S. Pat. No. 10,471,268, filed Oct. 13, 2015 / Nov. 12, 2019.
U.S. Appl. No. 14/939,955 / U.S. Pat. No. 9,981,122, filed Nov. 12, 2015 / May 29, 2018.
U.S. Appl. No. 15/202,435 / U.S. Pat. No. 9,950,159, filed Jul. 5, 2016 / Apr. 24, 2018.
U.S. Appl. No. 15/202,485 / U.S. Pat. No. 10,327,810, filed Jul. 5, 2016 / Jun. 25, 2019.
U.S. Appl. No. 15/299,399 / U.S. Pat. No. 10,016,603, filed Oct. 20, 2016 / Jul. 10, 2018.
U.S. Appl. No. 15/853,543 / U.S. Pat. No. 10,661,078, filed Dec. 22, 2017 / May 26, 2020.
U.S. Appl. No. 15/944,730 / U.S. Pat. No. 10,828,490, filed Apr. 3, 2018 / Nov. 10, 2020.
U.S. Appl. No. 15/948,945 / U.S. Pat. No. 10,449,355, filed Apr. 9, 2018 / Oct. 22, 2019.
U.S. Appl. No. 16/264,632 / U.S. Pat. No. 11,103,706, filed Jan. 31, 2019 / Aug. 31, 2021.
U.S. Appl. No. 16/443,819 / U.S. Pat. No. 11,406,421, filed Jun. 17, 2019 / Aug. 9, 2022.
U.S. Appl. No. 16/656,500 / U.S. Pat. No. 11,376,427, filed Oct. 17, 2019 / Jul. 5, 2022.
U.S. Appl. No. 16/817,574 / U.S. Pat. No. 10,926,083, filed Mar. 12, 2020 / Feb. 23, 2021.
U.S. Appl. No. 17/092,073, filed Nov. 6, 2020.
U.S. Appl. No. 17/173,121, filed Feb. 10, 2021.
U.S. Appl. No. 17/411,713 / U.S. Pat. No. 11,331,488, filed Aug. 25, 2021 / May 17, 2022.
U.S. Appl. No. 17/647,341 / U.S. Pat. No. 11,471,670, filed Jan. 6, 2022 / Oct. 18, 2022.
U.S. Appl. No. 17/660,375 / U.S. Pat. No. 11,679,261, filed Apr. 22, 2022 / Jun. 20, 2023.
U.S. Appl. No. 17/810,586, filed Jul. 1, 2022.
U.S. Appl. No. 17/812,981, filed Jul. 15, 2022.
U.S. Appl. No. 17/812,989 / U.S. Pat. No. 11,679,262, filed Jul. 15, 2022 / Jun. 20, 2023.
U.S. Appl. No. 17/816,519, filed Aug. 1, 2022.
U.S. Appl. No. 18/046,835, filed Oct. 14, 2022.
U.S. Appl. No. 18/186,149, filed Mar. 18, 2023.

* cited by examiner

FATIGUE-RESISTANT ELECTROSTIMULATION LEADS AND METHODS OF USE THEREOF

CROSS-REFERENCES TO RELATED APPLICATIONS

This application claims priority to U.S. Provisional Patent Application Ser. No. 63/366,132, filed Jun. 9, 2022, the entire contents of which are incorporated herein by reference.

FIELD OF USE

The present disclosure is directed to leads for providing neuromuscular electrical stimulation that enhance fatigue-resistance, methods of use thereof, and methods for manufacturing the same.

BACKGROUND

The human back is a complicated structure including bones, muscles, ligaments, tendons, nerves and other structures. The spinal column has interleaved vertebral bodies and intervertebral discs, and permits motion in several planes including flexion-extension, lateral bending, axial rotation, longitudinal axial distraction-compression, anterior-posterior sagittal translation, and left-right horizontal translation. The spine provides connection points for a complex collection of muscles that are subject to both voluntary and involuntary control.

Back pain in the lower or lumbar region of the back is common. In many cases, the cause of back pain is unknown. It is believed that some cases of back pain are caused by abnormal mechanics of the spinal column. Degenerative changes, injury of the ligaments, acute trauma, or repetitive microtrauma may lead to back pain via inflammation, biochemical and nutritional changes, immunological factors, changes in the structure or material of the endplates or discs, and pathology of neural structures.

The spinal stabilization system may be conceptualized to include three subsystems: 1) the spinal column, which provides intrinsic mechanical stability; 2) the spinal muscles, which surround the spinal column and provide dynamic stability; and 3) the neuromotor control unit, which evaluates and determines requirements for stability via a coordinated muscle response. In patients with a functional stabilization system, these three subsystems work together to provide mechanical stability. It is applicant's realization that low back pain results from dysfunction of these subsystems.

The spinal column consists of vertebrae and ligaments, e.g. spinal ligaments, disc annulus, and facet capsules. There has been an abundance of in-vitro work in explanted cadaver spines and models evaluating the relative contribution of various spinal column structures to stability, and how compromise of a specific column structure will lead to changes in the range of motion of spinal motion segments.

The spinal column also has a transducer function, to generate signals describing spinal posture, motions, and loads via mechanoreceptors present in the ligaments, facet capsules, disc annulus, and other connective tissues. These mechanoreceptors provide information to the neuromuscular control unit, which generates muscle response patterns to activate and coordinate the spinal muscles to provide muscle mechanical stability. Ligament injury, fatigue, and viscoelastic creep may corrupt signal transduction. If spinal column structure is compromised, due to injury, degeneration, or viscoelastic creep, then muscular stability must be increased to compensate and maintain stability.

Muscles provide mechanical stability to the spinal column. This is apparent by viewing cross section images of the spine, as the total area of the cross sections of the muscles surrounding the spinal column is larger than the spinal column itself. Additionally, the muscles have much larger lever arms than those of the intervertebral disc and ligaments.

Under normal circumstances, the mechanoreceptors exchange signals with the neuromuscular control unit for interpretation and action. The neuromuscular control unit produces a muscle response pattern based upon several factors, including the need for spinal stability, postural control, balance, and stress reduction on various spinal components.

It is believed that in some patients with back pain, the spinal stabilization system is dysfunctional. With soft tissue injury, mechanoreceptors may produce corrupted signals about vertebral position, motion, or loads, leading to an inappropriate muscle response. In addition, muscles themselves may be injured, fatigued, atrophied, or lose their strength, thus aggravating dysfunction of the spinal stabilization system. Conversely, muscles can disrupt the spinal stabilization system by going into spasm, contracting when they should remain inactive, or contracting out of sequence with other muscles. As muscles participate in the feedback loop via mechanoreceptors in the form of muscle spindles and golgi tendon organs, muscle dysfunction may further compromise normal muscle activation patterns via the feedback loops.

Trunk muscles may be categorized into local and global muscles. The local muscle system includes deep muscles, and portions of some muscles that have their origin or insertion on the vertebrae. These local muscles control the stiffness and intervertebral relationship of the spinal segments. They provide an efficient mechanism to fine-tune the control of intervertebral motion. The lumbar multifidus, with its vertebra-to-vertebra attachments is an example of a muscle of the local system. Another example is the transverse abdominus, with its direct attachments to the lumbar vertebrae through the thoracolumbar fascia. The thoracolumbar fascia is a deep investing membrane which covers the deep muscles of the back of the trunk. The thoracolumbar fascia includes superficial fascia and deep fascia. The superficial fascia is traditionally regarded as a layer of areolar connective or adipose tissue immediately beneath the skin, whereas deep fascia is a tougher, dense connective tissue continuous with it. Deep fascia is commonly arranged as sheets and typically forms a stocking around the muscles and tendons beneath it. Superficial fascia fibers run in the transverse direction, whereas deep fascia fibers run in a cranial-caudal direction.

The multifidus is the largest and most medial of the lumbar back muscles. It has a repeating series of fascicles which stem from the laminae and spinous processes of the vertebrae, and exhibit a constant pattern of attachments caudally. These fascicles are arranged in five overlapping groups such that each of the five lumbar vertebrae gives rise to one of these groups. At each segmental level, a fascicle arises from the base and caudolateral edge of the spinous process, and several fascicles arise, by way of a common tendon, from the caudal tip of the spinous process. Although confluent with one another at their origin, the fascicles in each group diverge caudally to assume separate attachments to the mamillary processes, the iliac crest, and the sacrum.

Some of the deep fibers of the fascicles that attach to the mamillary processes attach to the capsules of the facet joints next to the mamillary processes. The fascicles arriving from the spinous process of a given vertebra are innervated by the medial branch of the dorsal ramus that issues from below that vertebra. The dorsal ramus is part of spinal nerve roots formed by the union of dorsal root fibers distal to the dorsal root ganglion and ventral root fibers. The dorsal root ganglion is a collection of sensory neurons that relay sensory information from the body to the central nervous system.

The global muscle system encompasses the large, superficial muscles of the trunk that cross multiple motion segments, and do not have direct attachment to the vertebrae. These muscles are the torque generators for spinal motion, and control spinal orientation, balance the external loads applied to the trunk, and transfer load from the thorax to the pelvis. Global muscles include the oblique internus abdominus, the obliquus externus abdmonimus, the rectus abdominus, the lateral fibers of the quadratus lumborum, and portions of the erector spinae.

Normally, load transmission is painless. Over time, dysfunction of the spinal stabilization system is believed to lead to instability, resulting in overloading of structures when the spine moves beyond its neutral zone. The neutral zone is a range of intervertebral motion, measured from a neutral position, within which the spinal motion is produced with a minimal internal resistance. High loads can lead to inflammation, disc degeneration, facet joint degeneration, and muscle fatigue. Since the endplates and annulus have a rich nerve supply, it is believed that abnormally high loads may be a cause of pain. Load transmission to the facets also may change with degenerative disc disease, leading to facet arthritis and facet pain.

Functional electrical stimulation (FES) is the application of electrical stimulation to cause muscle contraction to re-animate limbs following damage to the nervous system such as with stroke or spine injury. FES has been the subject of much prior art and scientific publications. In FES, the goal generally is to bypass the damaged nervous system and provide electrical stimulation to nerves or muscles directly which simulates the action of the nervous system. One lofty goal of FES is to enable paralyzed people to walk again, and that requires the coordinated action of several muscles activating several joints. The challenges of FES relate to graduation of force generated by the stimulated muscles, and the control system for each muscle as well as the system as a whole to produce the desired action such as standing and walking.

With normal physiology, sensors in the muscle, ligaments, tendons and other anatomical structures provide information such as the force a muscle is exerting or the position of a joint, and that information may be used in the normal physiological control system for limb position and muscle force. This sense is referred to as proprioception. In patients with spinal cord injury, the sensory nervous system is usually damaged as well as the motor system, and thus the afflicted person loses proprioception of what the muscle and limbs are doing. FES systems often seek to reproduce or simulate the damaged proprioceptive system with other sensors attached to a joint or muscle. FES has also been used to treat spasticity, characterized by continuous increased muscle tone, involuntary muscle contractions, and altered spinal reflexes which leads to muscle tightness, awkward movements, and is often accompanied by muscle weakness. Spasticity results from many causes including cerebral palsy, spinal cord injury, trauma, and neurodegenerative diseases.

Neuromuscular Electrical Stimulation (NMES) is a subset of the general field of electrical stimulation for muscle contraction, as it is generally applied to nerves and muscles which are anatomically intact, but malfunctioning in a different way. NMES may be delivered via an external system or, in some applications, via an implanted system. NMES via externally applied skin electrodes has been used to rehabilitate skeletal muscles after injury or surgery in the associated joint. This approach is commonly used to aid in the rehabilitation of the quadriceps muscle of the leg after knee surgery. Electrical stimulation is known to not only improve the strength and endurance of the muscle, but also to restore malfunctioning motor control to a muscle. See, e.g., Gondin et al., "Electromyostimulation Training Effects on Neural Drive and Muscle Architecture", Medicine & Science in Sports & Exercise 37, No. 8, pp. 1291-99 (August 2005).

The goals and challenges of rehabilitation of anatomically intact (i.e., non-pathological) neuromuscular systems are fundamentally different from the goals and challenges of FES for treating spinal injury patients or people suffering from spasticity. In muscle rehabilitation, the primary goal is to restore normal functioning of the anatomically intact neuromuscular system, whereas in spinal injury and spasticity, the primary goal is to simulate normal activity of a pathologically damaged neuromuscular system.

U.S. Pat. Nos. 8,428,728 and 8,606,358 to Sachs, both assigned to the assignee of the present disclosure, and both incorporated herein in their entireties by reference, describe implanted electrical stimulation devices that are designed to restore neural drive and rehabilitate the multifidus muscle to improve stability of the spine. Rather than masking pain signals while the patient's spinal stability potentially undergoes further deterioration, the stimulator systems described in those applications are designed to reactivate the motor control system and/or strengthen the muscles that stabilize the spinal column, which in turn is expected to reduce persistent or recurrent pain.

While the stimulator systems described in the Sachs patents seek to rehabilitate the multifidus and restore neural drive, use of those systems necessitates the implantation of one or more electrode leads in the vicinity of a predetermined anatomical site, such as the medial branch of the dorsal ramus of the spinal nerve to elicit contraction of the lumbar multifidus muscle. For lead implantation using the Seldinger technique, it has been proposed to insert a needle in the patient's back, insert a guidewire through a lumen in the needle, remove the needle, insert a sheath over the guidewire, remove the guidewire, insert the electrode lead through a lumen of the sheath, and remove the sheath. Such a process can result in complications depending on the insertion site due to anatomical structures surrounding the target implantation site, impeding the insertion path. For example, as discussed above, the deep back muscles are covered by the thoracolumbar fascia which comprises superficial fascia running in the transverse direction and deep fascia running in a cranial-caudal direction. There is a risk that electrode lead conductors may experience a tight bend near the location where the lead enters the thoracolumbar fascia when the lead is inserted within the body near the lateral edge of the spine. Such a tight bend may lead to dislodgement of the electrode lead and/or fracture, thereby preventing proper therapy delivery. The difference in directions of the superficial and deep fascia near the insertion site at the lateral edge of the spine may increase the risk of a high stress location on the lead, as described in U.S. Pat. No.

10,327,810 to Shiroff, assigned to the assignee of the present disclosure, and incorporated herein in its entirety by reference.

Moreover, the muscles of the lower back are highly mobile and create an environment that can impose large mechanical stresses on electrode leads, resulting in a high risk of lead dislodgement and/or lead fracture. As a result, fracture-inducing shear forces as well as axial forces imposed on a conventional lead by the relative movement of the muscles overlying the back muscles targeted for stimulation may cause the lead to dislodge and/or fracture.

Conventional medical leads generally include multiple conductors that carry electrical signals from a medical device coupled to the proximal end of the lead to one or more electrodes at the distal end of the lead. Various medical leads have been designed to reduce the risk of lead fracture. For example, U.S. Pat. No. 9,242,089 to Klardie describes medical leads having coiled filars (conductors) that have longitudinally straight ends, e.g., where the electrical connectors are present for connection between the filars and the medical device. Specifically, the filars of the medical lead of Klardie have a coiled configuration along the entire length of the lead except at the ends of the lead.

Moreover, U.S. Pat. No. 4,608,986 to Beranek describes leads having an improved straight wire conductor that extends loosely and slidably through the lumen of the lead, and is made of a nickel and titanium alloy to minimize stress and fatigue on the wire conductors. Similarly, U.S. Pat. No. 5,760,341 to Laske describes the benefit of medical leads having a straight wire configuration over a coil configuration.

In view of the foregoing drawbacks of previously known medical leads, there exists a need for electrostimulation leads with enhanced fatigue-resistance, specifically, to endure fracture-inducing shear forces caused by movement of highly mobile lower back muscles during neuromuscular electrical stimulation to treat back pain.

SUMMARY

The present disclosure overcomes the drawbacks of previously-known systems and methods by providing a lead for neuromuscular electrical stimulation of a patient. The lead may include a lead body having a proximal region, a distal region, and a fatigue-resistant zone disposed between the proximal region and the distal region. The lead body may be structured to be implanted adjacent to nervous tissue associated with control of a lumbar spine. In addition, the lead may include one or more electrodes disposed on the distal region of the lead body, and one or more conductors electrically coupled to the one or more electrodes and extending through the lead body from the distal region to the proximal region. The one or more electrodes may stimulate a dorsal ramus nerve, or fascicles thereof, that innervate a multifidus muscle.

The one or more conductors may be formed of individual strands that extend substantially parallel to a longitudinal axis of the lead body outside of the fatigue-resistant zone; whereas, within the fatigue-resistant zone, the individual strands of the one or more conductors may be wound in a coiled configuration within the lead body to enhance fatigue-resistance. For example, the individual strands of the one or more conductors may extend from the distal region substantially parallel to the longitudinal axis of the lead body to the fatigue-resistant zone, and extend from the fatigue-resistant zone substantially parallel to the longitudinal axis of the lead body to the proximal region. Accordingly, the fatigue-resistant zone may be disposed at a location within the patient that experiences fracture-inducing shear forces caused by movement of a patient's lower back muscles. In some embodiments, the lead body includes multiple fatigue-resistant zones. In addition, a portion of the one or more conductors that extends substantially parallel to the longitudinal axis of the lead body may have a length larger than a length of the fatigue-resistant zone.

The lead body may further include an insulated tube extending from the proximal region to the distal region, such that the one or more conductors extend within the insulated tube. Each of the one or more conductors may be individually insulated to provide a unique electrically conductive pathway. Additionally, each of the one or more conductors may be formed of a plurality of wires, e.g., seven wires.

The lead further may include a first fixation element coupled to the lead body proximal to at least one of the one or more electrodes. For example, the first fixation element may anchor the lead to an anchor site, e.g., muscle tissue associated with control of the lumbar spine. In addition, the lead may include a second fixation element coupled to the lead body distal to the first fixation element, wherein the first fixation element is angled distally relative to the lead body and the second fixation element is angled proximally relative to the lead body in a deployed state. Accordingly, the first and second fixation elements may sandwich the anchor site therebetween. In some embodiments, at least one of the one or more electrodes may be disposed between the first and second fixation elements.

In accordance with another aspect of the present disclosure, a system for neuromuscular electrical stimulation of a patient is provided. The system may include the lead for neuromuscular electrical stimulation of a patient, as well as a pulse generator that may be electrically coupled to the one or more electrodes via the one or more conductors. For example, the pulse generator may deliver electrical stimulation to the nervous tissue associated with control of the lumbar spine via the one or more electrodes. In some embodiments, the pulse generator may be implantable.

In accordance with yet another aspect of the present disclosure, a method for manufacturing the electrostimulation lead is provided. The method may include electrically coupling a distal end of one or more conductors to one or more electrodes disposed at a distal region of the electrostimulation lead; electrically coupling a proximal end of the one or more conductors to one or more contacts disposed at a proximal region of the electrostimulation lead; wounding a portion of the one or more conductors in a coiled configuration to form a fatigue-resistant zone of the electrostimulation lead, the fatigue-resistant zone structured to be disposed at a location within the patient that experiences fracture-inducing shear forces caused by movement of a patient's lower back muscles; and encapsulating the one or more conductors with an insulated tube, wherein the one or more conductors are formed of individual strands that extend substantially parallel to a longitudinal axis of the lead body outside of the fatigue-resistant zone.

In accordance with another aspect of the present disclosure, a method for implanting the electrostimulation lead within a patient is provided. The method may include providing an electrostimulation lead having a proximal region, a distal region, a fatigue-resistant zone disposed between the proximal region and the distal region, and one or more conductors formed of individual strands that extend from the distal region to the proximal region substantially parallel to a longitudinal axis of the electrostimulation lead outside of the fatigue-resistant zone; and implanting the distal region of the electrostimulation lead adjacent to nervous tissue associated with control of a lumbar spine such that the fatigue-resistant zone of the electrostimulation lead is disposed at a location within the patient that experiences fracture-inducing shear forces caused by movement of the patient's lower back muscles, wherein the individual strands of one or more conductors are wound in a coiled configuration within the fatigue-resistant zone to enhance fatigue-resistance.

In addition, the method may include coupling the proximal region of the electrostimulation lead to a pulse generator; and delivering electrical stimulation from the pulse generator to the nervous tissue associated with control of the lumbar spine via one or more electrodes disposed at the distal region of the electrostimulation lead. In some embodiments, the method may include implanting the pulse generator within the patient.

DETAILED DESCRIPTION

The electrostimulation lead of the stimulator systems described herein is a high fatigue-resistant lead with low electrical resistance. Specifically, the conductor(s) of the lead are coiled only in regions of the lead that are positioned adjacent high stress zone(s) within the patient, e.g., due to highly mobile lower back muscles during neuromuscular electrical stimulation, thereby limiting the amount of conductor coil required in the lead and reducing manufacturing costs. Moreover, the portions of the conductor(s) in their native straight configuration, e.g., extending parallel to the longitudinal axis of the lead, outside the high-fatigue resistant coiled portions of the lead may also facilitate manufacturability and provide a more robust design.

Figure 1:
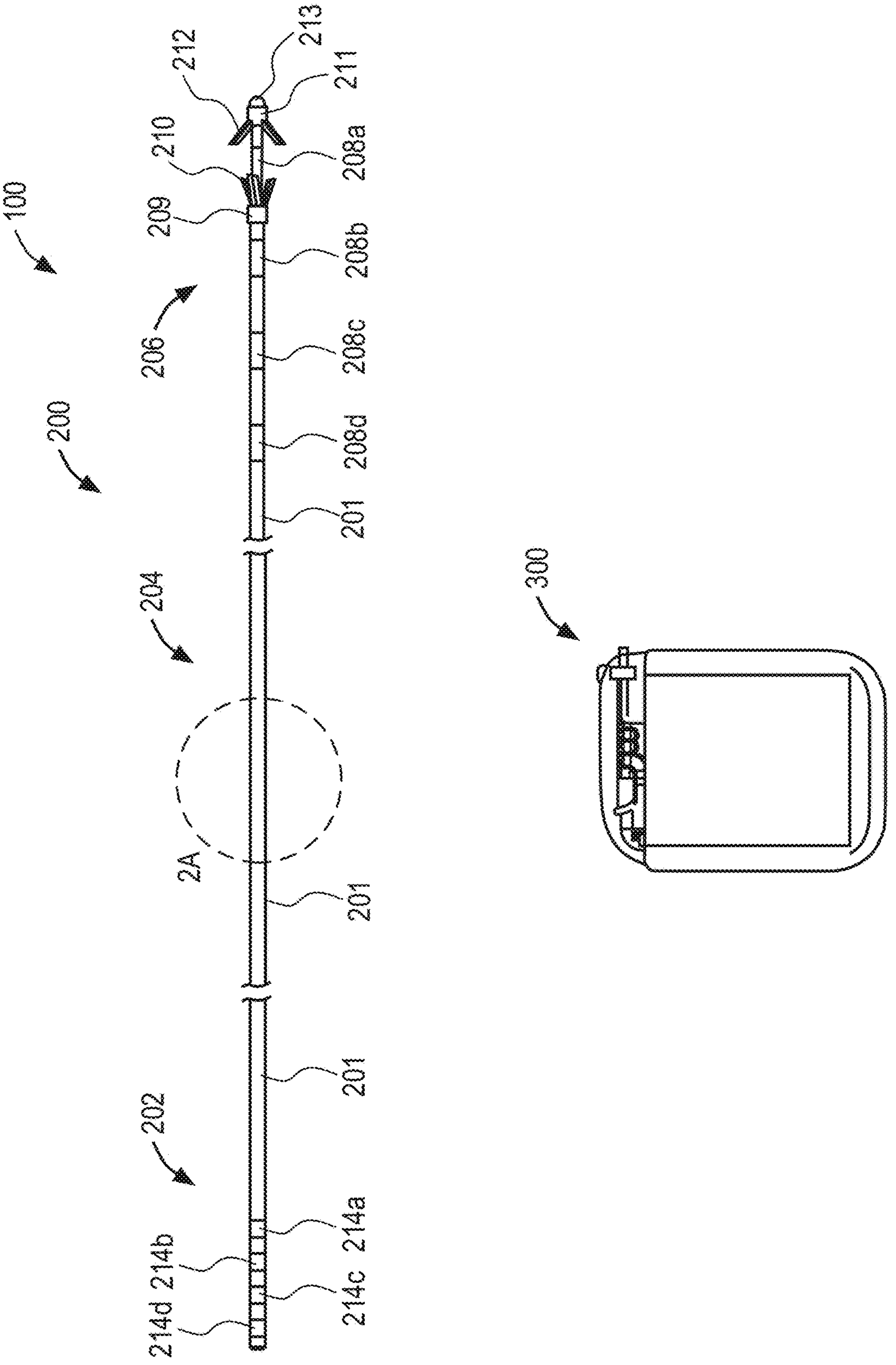
FIG. 1 is a schematic view of an exemplary embodiment of a stimulator system constructed in accordance with the principles of the present disclosure.

Referring now to FIG. 1, an exemplary stimulation system is provided. In FIG. 1, components of the system are not depicted to scale on either a relative or absolute basis. Stimulation system 100 may be constructed similar to the stimulation systems described in U.S. Pat. No. 9,950,159 to Beck, the entire contents of which are incorporated herein by reference. For example, stimulation system 100 includes electrostimulation lead 200 and pulse generator 300, which may be actuated via an actuator, an external programmer, and a software-based programming system.

Electrostimulation lead 200 includes lead body 201 having a plurality of electrodes, illustratively, electrodes 208*a*, 208*b*, 208*c*, 208*d*, disposed at distal region 206, the plurality of electrodes electrically coupled to a plurality of contacts, illustratively contacts 214*a*, 214*b*, 214*c*, 214*d*, disposed at proximal region 202, via a plurality of conductors as described in further detail below. Electrostimulation lead 200 is configured for implantation in or adjacent to tissue, e.g., nervous tissue, muscle, a ligament, and/or a joint capsule including tissue associated with local segmental control of the lumbar spine.

Lead body 201 is a suitable length for positioning the electrodes in or adjacent to target tissue while pulse generator 300 is implanted in a suitable location, e.g., the lower back. For example, lead body 201 may be between about 30 and 80 cm in length, and preferably about or about 65 cm in length. Lead body 201 is also of a suitable diameter for placement, for example, between about 1 and 2 mm in diameter and preferably about 1.3 mm. Electrodes 208*a*, 208*b*, 208*c*, 208*d* may be configured to stimulate the tissue at a stimulation frequency and at a level and duration sufficient to cause muscle to contract and may be ring electrodes, partial electrodes, segmented electrodes, nerve cuff electrodes placed around the nerve innervating the target muscle, or the like. Electrodes 208*a*, 208*b*, 208*c*, 208*d* are a suitable length(s) and spaced apart a suitable distance along lead body 201. For example, electrodes 208*a*, 208*b*, 208*c*, 208*d* may be about 2-5 mm in length, and preferably about 3 mm, and may be spaced apart about 2-6 mm, and preferably about 4 mm. As will also be understood by one of skill in the art, an electrode lead may contain more or fewer than four electrodes.

As shown in FIG. 1, first and second fixation elements 210 and 212 may be coupled to lead body 201 at distal region 206 via first and second fixation rings 209 and 211, respectively. First and second fixation elements 210 and 212 are configured to sandwich an anchor site, e.g., muscle, therebetween to secure electrostimulation lead 200 at a target site without damaging the anchor site. In the illustrated embodiment, first fixation elements 210 are positioned between electrode 208*b* and distal most electrode 208*a* and second fixation element 212 is positioned between distal most electrode 208*a* and end cap 213. The length of and spacing between the fixation elements is defined by the structure around which they are to be placed. In one embodiment, the length of each fixation element is between about 1.5-4 mm and preferably about 2.5 mm and the spacing is between about 2 mm and 10 mm and preferably about 6 mm. First and second fixation elements 210 and 212 are configured to collapse inward toward lead body 201 in a delivery state and to expand, e.g., due to retraction of a sheath, in a deployed state.

As shown in FIG. 1, first fixation elements 210 may be radially offset with respect to second fixation elements 212. For example, first fixation elements 210 may be configured to be radially offset relative to second fixation elements 212 by prefabricating at least one of first fixation ring 209 and second fixation ring 211 relative to lead body 201 such that at least one of first and second fixation elements 210 and 212 is radially offset with respect to each other. For example, the projections of first fixation elements 210 may be radially offset relative to the projections of second fixation elements 212 by, e.g., approximately 60 degrees. Moreover, first and second fixation elements 210 and 212 may be formed of a flexible material, e.g., a polymer, and may be collapsible and self-expandable when deployed. For example, first and second fixation elements 210 and 212 may collapse inward toward lead body 201 in a delivery state such that they are generally parallel to the longitudinal axis of lead body 201 within a sheath. In the delivery state, the radially offset first and second fixation elements 210 and 212 need not overlap within a sheath.

Further, first and second fixation elements 210 and 212 may expand, e.g., due to retraction of the sheath, in a deployed state. In the deployed state, first fixation elements 210 may be angled distally relative to lead body 202, and resist motion in the first direction and prevent, in the case illustrated, insertion of the lead too far, as well as migration distally. Second fixation elements 212 may be angled proximally relative to lead body 201 and penetrate through a tissue plane and deploy on the distal side of the tissue immediately adjacent to the target of stimulation. First fixation elements 210 are configured to resist motion in the opposite direction relative to second fixation elements 212. This combination prevents migration both proximally and distally, and also in rotation.

While FIG. 1 illustrates fixation elements 210 and 212 on lead body 201, it should be understood that other fixation elements may be used to anchor electrode lead 200 at a suitable location including the fixation elements described in U.S. Pat. No. 9,079,019 to Crosby and U.S. Pat. No. 9,999,763 to Shiroff, both assigned to the assignee of the present disclosure, the entire contents of each of which are incorporated herein by reference.

Lead body 201 further may include a stylet lumen (not shown) extending therethrough. The stylet lumen may be shaped and sized to permit a stylet to be inserted therein, for example, during delivery of electrostimulation lead 200. In one embodiment, end cap 213 is used to prevent the stylet from extending distally out of the stylet lumen beyond end cap 213.

As shown in FIG. 1, electrostimulation lead 200 may include contacts 214*a*, 214*b*, 214*c*, 214*d* at proximal region 202 separated along lead body 201 by a plurality of spacers, e.g., insulated tubing. Contacts 214*a*, 214*b*, 214*c*, 214*d* may comprise an isodiametric terminal and are electrically coupled to electrodes 208*a*, 208*b*, 208*c*, 208*d*, respectively, via, for example, individually coated wires extending between the contacts and electrodes as described in further detail below. A portion of proximal region 202 may be configured to be inserted in pulse generator 300.

Electrostimulation lead 200 may be coupled to pulse generator 300. Pulse generator 300 may be disposed external to the patient during operation of system 100. Alternatively, pulse generator 300 may be implanted within the patient, e.g., an implantable pulse generator (IPG). For example, pulse generator 300 may be implanted within the lower back of the patient. Pulse generator 300 is configured to generate pulses such that electrodes 208*a*, 208*b*, 208*c*, and/or 208*d* deliver neuromuscular electrical stimulation ("NMES") to target tissue. In one embodiment, the electrodes are positioned to stimulate a peripheral nerve where the nerve enters skeletal muscle, which may be one or more of the multifidus, transverse abdominus, quadratus lumborum, psoas major, internus abdominus, obliquus externus abdominus, and erector spinae muscles. Such stimulation may induce contraction of the muscle to restore neural control and rehabilitate the muscle, thereby improving muscle function of local segmental muscles of the lumbar spine, improving lumbar spine stability, and reducing back pain.

Exemplary stimulation parameters in accordance with aspects of the present disclosure are now described. Preferably, such stimulation parameters are selected and programmed to induce contraction of muscle to restore neural control and rehabilitate muscle associated with control of the spine, thereby improving lumbar spine stability and reducing back pain. As used in this specification, "to restore muscle function" means to restore an observable degree of muscle function as recognized by existing measures of patient assessment, such as the Oswestry Disability Index ("ODI") as described in Lauridsen et al., *Responsiveness and minimal clinically important difference for pain and disability instruments in low back pain patients*, BMC Musculoskeletal Disorders, 7: 82-97 (2006), the European Quality of Life Assessment 5D ("EQ-5D") as described in Brazier et al., *A comparison of the EQ-5D and SF-6D across seven patient groups*, Health Econ. 13: 873-884 (2004), or a Visual Analogue Scale ("VAS") as described in Hagg et al., *The clinical importance of changes in outcome scores after treatment for chronic low back pain*, Eur Spine J 12: 12-20 (2003). In accordance with one aspect of the present disclosure, "to restore muscle function" means to observe at least a 15% improvement in one of the foregoing assessment scores within 30-60 days of initiation of treatment. The stimulation parameters may be programmed into pulse generator 300, and/or may be adjusted in the pulse generator 300 responsive to (i) stimulation commands transferred from the activator or (ii) programming data transferred from the external programmer.

The stimulation parameters include, for example, pulse amplitude (voltage or current), pulse width, stimulation rate, stimulation frequency, ramp timing, cycle timing, session timing, and electrode configuration, including commands to start or stop a treatment session. In one embodiment, pulse amplitude is programmed to be adjustable between 0 and 7 mA. In a preferred embodiment, pulse amplitude is programmed to be between about 2-5 mA, 2.5-4.5 mA, or 3-4 mA, and preferably about 3.5 mA. In one embodiment, pulse width is programmed to be adjustable between 25 and 500 µs. In a preferred embodiment, pulse width is programmed to be between about 100-400 µs, 150-350 µs, or 200-300 µs, and preferably about 350 µs. In one embodiment, stimulation rate is programmed to be adjustable between 1 and 40 Hz. In a preferred embodiment, stimulation rate is programmed to be between about 5-35 Hz, 10-30 Hz, or 15-20 Hz, and preferably about 20 Hz. In one embodiment, on ramp timing is programmed to be adjustable between 0 and 5 s. In a preferred embodiment, on ramp timing is programmed to be between about 0.5-4.5 s, 1-4 s, 1.5-3.5 s, or 2-3 s, and preferably about 2.5 s. In one embodiment, off ramp timing is programmed to be adjustable between 0 and 5 s. In a preferred embodiment, off ramp timing is programmed to be between about 0.5-4.5 s, 1-4 s, 1.5-3.5 s, or 2-3 s, and preferably about 2.5 s. In one embodiment, cycle-on timing is programmed to be adjustable between 2 and 20 s. In a preferred embodiment, cycle-on timing is programmed to be between about 4-18 s, 6-16 s, 8-14 s, 9-13 s, or 10-12 s and preferably about 10 s. In one embodiment, cycle-off timing is programmed to be adjustable between 20 and 120 s. In a preferred embodiment, cycle-off timing is programmed to be between about 30-110 s, 40-100 s, s, 55-85 s, 60-80 s, or 65-75 s and preferably about 70 s. In one embodiment, session timing is programmed to be adjustable between 1 and 60 min. In a preferred embodiment, session timing is programmed to be between about 5-55 min, 10-50 min, 15-45 min, 20-40 min, or 25-35 min, and preferably about 30 min.

Figure 2A:
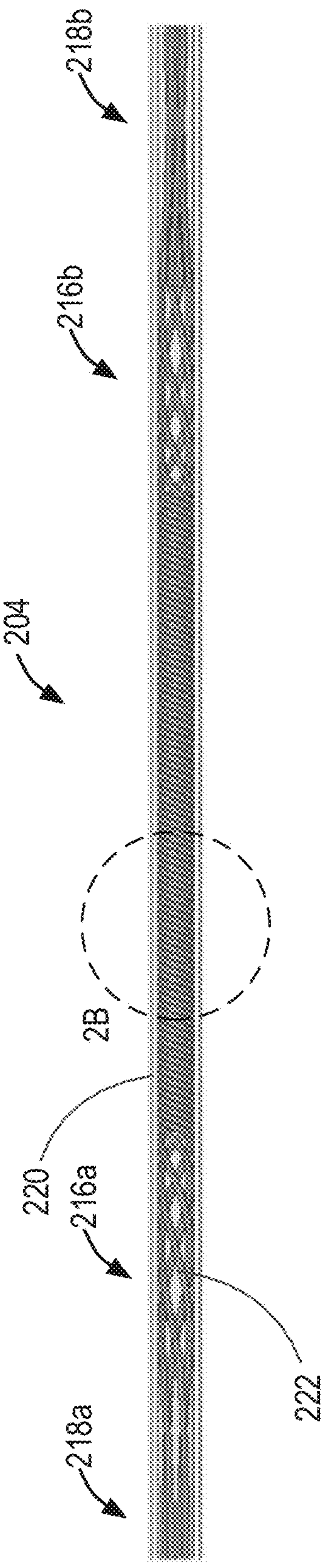
FIG. 2A is a close-up view of a fatigue-resistant zone of the electrostimulation lead of the stimulator system of FIG. 1.
Figure 2B:
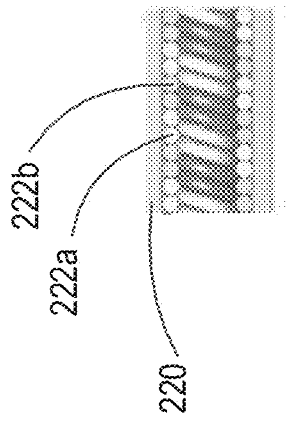
FIG. 2B is a close-up view of the coiled configuration of the conductors within the fatigue-resistant zone of FIG. 2A.
Figure 2C:
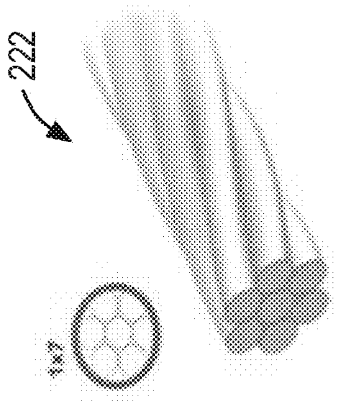
FIG. 2C is a close-up view of an individual strand of a conductor constructed in accordance with the principles of the present disclosure.

Referring now to FIGS. 2A to 2C, fatigue-resistant zone 204 of electrostimulation lead 200 is described in further detail. As described above, contacts 214*a*, 214*b*, 214*c*, 214*d* may be electrically coupled to electrodes 208*a*, 208*b*, 208*c*, 208*d*, respectively, via, individually insulated/coated wires, e.g., one or more conductors 222, extending between the contacts at proximal region 202 and the electrodes at distal region 206. As shown in FIG. 2A, conductors 222 may be encapsulated within flexible, insulated tube 220 to form lead body 201, such that conductors 222 extend from proximal region 202 to distal region 206 within insulated tube 220. Conductors 222 may extend generally parallel along the longitudinal axis of lead body 201 within insulated tube 220, e.g., along straight wire portions 218*a* and 218*b*, except at fatigue-resistant zone 204. At fatigue-resistant zone 204, conductors 222 may be wounded in a coiled configuration to enhance fatigue-resistance. For example, as shown in FIG. 2A, conductors 222 extend generally parallel along the longitudinal axis of lead body 201 in a straight wire configuration at straight wire portion 218*a*, transition to a coiled configuration at transition portion 216*a*, maintain a coiled configuration along fatigue-resistant zone 204, transition back to a straight wire configuration at transition portion 216*b*, and extend generally parallel along the longitudinal axis of lead body 201 in a straight wire configuration at straight wire portion 218*b*. As conductors 222 are only coiled at fatigue-resistant zone 204, less wire will be required to form electrostimulation lead 200 compared with a conventional lead. Accordingly, straight wire portions 218*a* and 218*b* may have a combined length that is significantly larger than the length of fatigue-resistant zone 204.

Fatigue-resistant zone 204 may be positioned along electrostimulation lead 200 at a position between proximal region 202 and distal region 204 of lead body 201, such that fatigue-resistant zone 204 is aligned with a predetermined high stress zone(s) within the patient when electrostimulation lead 200 is implanted within the patient. A high stress zone is defined herein by an area within the patient that experiences high stress due to highly mobile lower back muscles during neuromuscular electrical stimulation, thereby subjecting an implanted lead to fracture-inducing shear forces. Upon determination of such high stress zone(s) within the patient, electrostimulation lead 200 may be selected such that fatigue-resistant zone 204 is aligned with the predetermined high stress zone(s) within the patient when electrostimulation lead 200 is implanted within the patient.

As will be understood by a person having ordinary skill in the art, a patient may have more than one high stress zone, and thus, electrostimulation lead 200 may include a corresponding number of fatigue-resistant zones. For example, conductors 222 extend generally parallel along the longitudinal axis of lead body 201 in a straight wire configuration at a first straight wire portion extending from proximal region 202, transition to a coiled configuration at a first transition portion, maintain a coiled configuration along a first fatigue-resistant zone, transition back to a straight wire configuration at a second transition portion, extend generally parallel along the longitudinal axis of lead body 201 in a straight wire configuration at a second straight wire portion, transition to a coiled configuration at a third transition portion, maintain a coiled configuration along a second fatigue-resistant zone, transition back to a straight wire configuration at a fourth transition portion, extend generally parallel along the longitudinal axis of lead body 201 in a straight wire configuration at a third straight wire portion towards distal region 206.

As shown in FIG. 2B, conductors 222 may include more than one individually insulated wire. In the illustrated embodiment, conductors 222 include first conductor 222*a* and second conductor 222*b*. Each individually insulated wire may provide a unique electrically conductive pathway between the contacts and electrodes of electrostimulation lead 200. Accordingly, when electrostimulation lead 200 includes four electrodes and four contacts, four individually insulated wires may be used to electrically coupled the contacts and the electrodes. Alternatively, as shown in FIG. 2B, two individually insulated wires may be used to electrically coupled four contacts to four electrodes.

As shown in FIG. 2C, each individually insulated wires of conductors 222 may be formed by a plurality of individual wires, e.g., seven wires, helically wound together to provide further fatigue-resistance. As will be understood by a person having ordinary skill in the art, the plurality of individual wires forming the individually insulated wires of conductors 222 may include more or less than seven wires.

Figure 3:
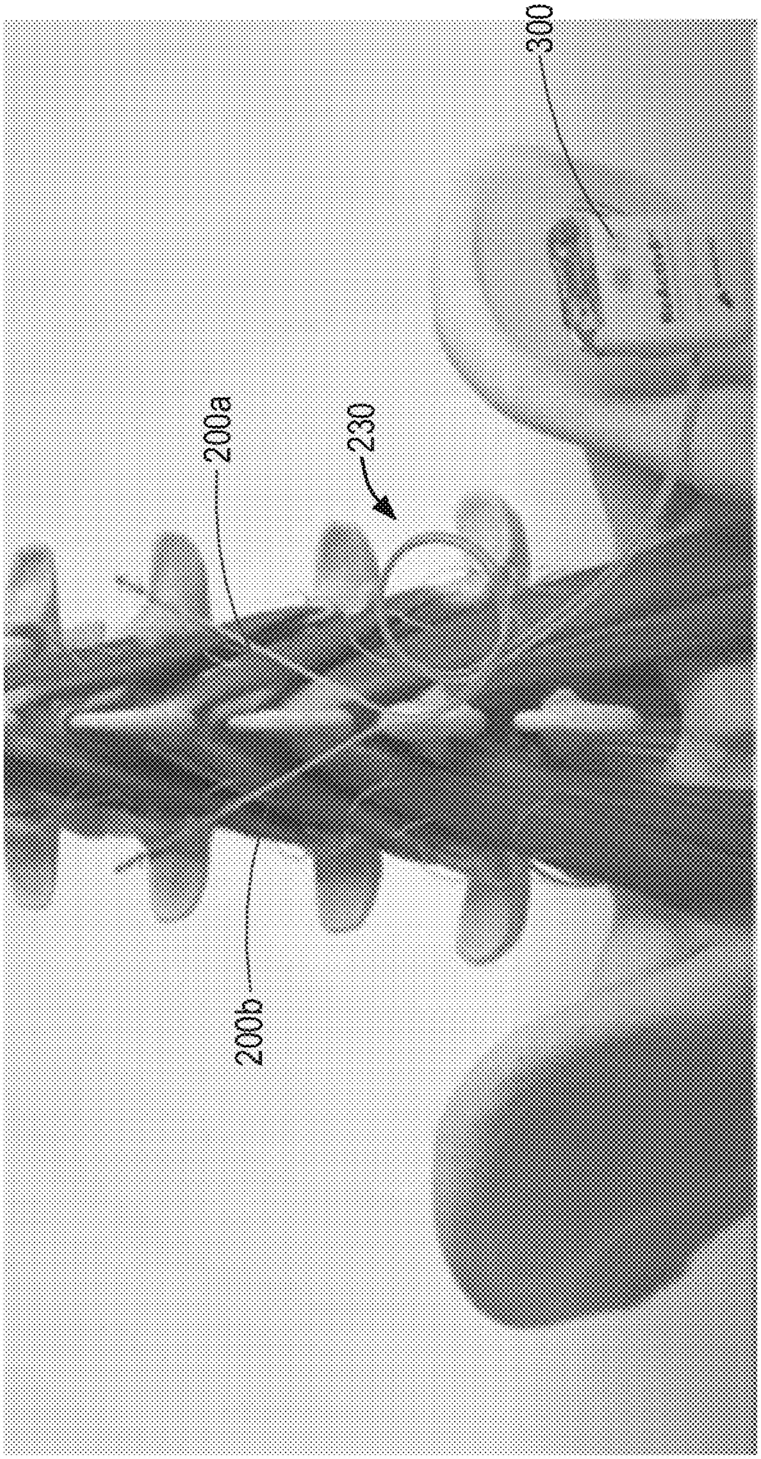
FIG. 3 illustrates the stimulator system of FIG. 1 implanted within a patient with two electrostimulation leads in accordance with the principles of the present disclosure.

FIG. 3 illustrates stimulation system 100 implanted within a patient. As shown in FIG. 3, multiple electrostimulation leads, e.g., leads 200*a* and 200*b*, may be coupled to pulse generator 300, and may be implanted in or adjacent to tissue, e.g., nervous tissue, muscle, a ligament, and/or a joint capsule including tissue associated with local segmental control of the lumbar spine, e.g., on opposite sides of the spine. Moreover, as shown in FIG. 3, electrode stimulation leads 200*a* and 200*b* may be implanted with strain relief loop 230 positioned between proximal region 202 and distal region 206, as described in U.S. Pat. No. 10,195,419 to Shiroff, the entire contents of which are incorporated herein by reference. Strain relief loop 230 is configured to reduce transmission of axial and lateral loads applied to lead body 201 of the respective electrostimulation lead to distal region 206 and the anchoring mechanism, e.g., first and second fixation elements 210 and 212, to prevent lead dislodgement from the tissue associated with control of the lumbar spine.

Figure 4:
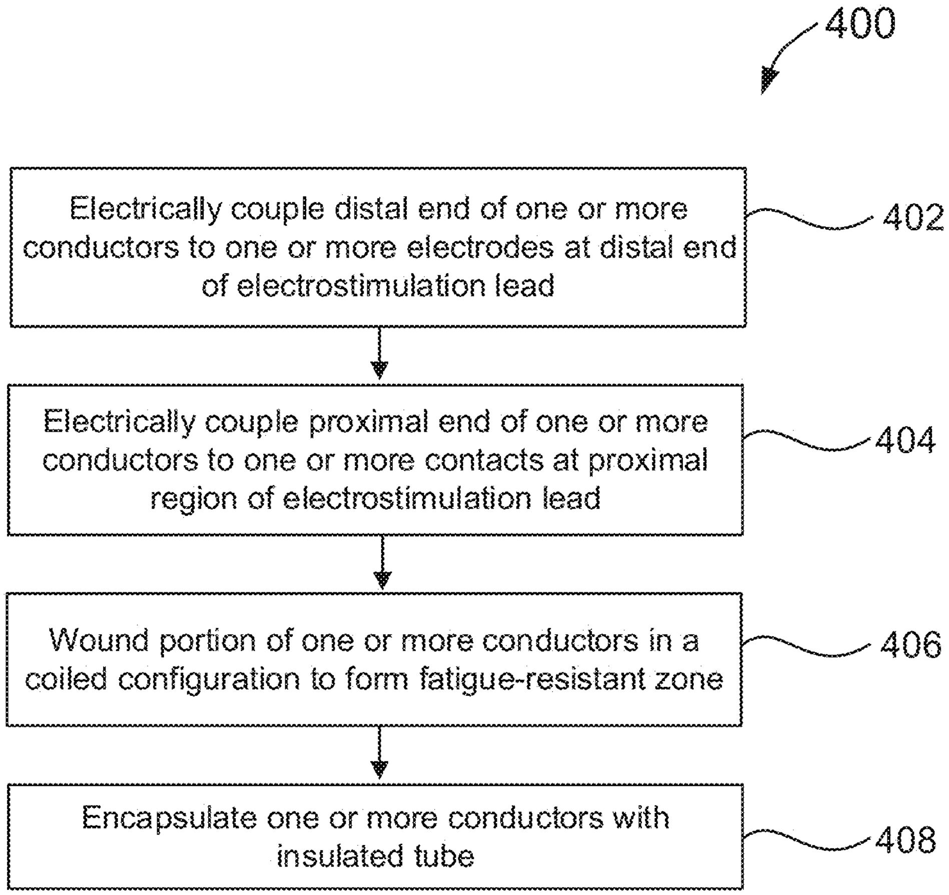
FIG. 4 is a flow chart of exemplary method steps for manufacturing the electrostimulation lead of FIG. 2 in accordance with the principles of the present disclosure.

Referring now to FIG. 4, exemplary method 400 for manufacturing electrostimulation lead 200 is provided. For example, at step 402, the distal end of one or more conductors 222 may be electrically coupled to one or more electrodes, e.g., electrodes 208*a*, 208*b*, 208*c*, 208*d*, of electrostimulation lead 200. At step 404, the proximal end of one or more conductors 222 may be electrically coupled to one or more contacts, e.g., contacts 214*a*, 214*b*, 214*c*, 214*d*, of electrostimulation lead 200. At step 406, one or more conductors 222 may be wound in a coiled configuration to form one or more fatigue-resistant zones, e.g., fatigue-resistant zone 204, corresponding to one or more predetermined high stress zone(s) within the patient's lower back. At step 408, one or more conductors 222 may be encapsulated within insulated tube 220. As will be understood by a person having ordinary skill in the art, the method steps described above may be performed in any order to manufacture electrostimulation lead 200. For example, one or more conductors 222 may be encapsulated within insulated tube 408 in a straight wire configuration, and then select portion(s) of conductors 222 may be wound into a coiled configuration to form one or more fatigue-resistant zones 204 within insulated tube 408.

While various illustrative embodiments of the disclosure are described above, it will be apparent to one skilled in the art that various changes and modifications may be made therein without departing from the disclosure. The appended claims are intended to cover all such changes and modifications that fall within the true scope of the disclosure.

What is claimed:

1. A lead for neuromuscular electrical stimulation of a patient, the lead comprising:

a lead body having a proximal region, a distal region, and a fatigue-resistant zone disposed between the proximal region and the distal region, the lead body configured to be implanted adjacent to nervous tissue associated with control of a lumbar spine;

at least one electrode disposed on the distal region of the lead body; and at least one conductor electrically coupled to the at least one electrode and extending through the lead body from the distal region to the proximal region, the at least one conductor comprising individual strands that extend in a straight configuration parallel to a longitudinal axis of the lead body outside of the fatigue-resistant zone, wherein, within the fatigue-resistant zone, the individual strands of the at least one conductor are tightly wound in a coiled configuration within the lead body to enhance fatigue-resistance at the fatigue-resistant zone, the fatigue-resistant zone configured to be disposed at a location within the patient that experiences fracture-inducing shear forces caused by movement of a patient's lower back muscles post-implantation, and wherein the individual strands of the at least one conductor are maintained in the coiled configuration within the fatigue-resistant zone and gradually transition towards the straight configuration in a semi-coiled configuration within a first transition portion proximal to the fatigue-resistant zone to thereby extend in the straight configuration outside of the fatigue-resistant zone towards the proximal region, and within a second transition portion distal to the fatigue-resistant zone to thereby extend in the straight configuration outside of the fatigue-resistant zone towards the distal region.

2. The lead of claim 1, wherein the lead body comprises an insulated tube extending from the proximal region to the distal region, and wherein the at least one conductor extends within the insulated tube.

3. The lead of claim 1, wherein the lead body comprises multiple fatigue-resistant zones.

4. The lead of claim 1, wherein each of the at least one conductor is individually insulated to provide a unique electrically conductive pathway.

5. The lead of claim 1, wherein each of the at least one conductor comprises a plurality of wires.

6. The lead of claim 5, wherein each of the at least one conductor comprises seven wires.

7. The lead of claim 1, wherein a portion of the at least one conductor that extends parallel to the longitudinal axis of the lead body comprises a length larger than a length of the fatigue-resistant zone.

8. The lead of claim 1, wherein the individual strands of the at least one conductor extend from the distal region parallel to the longitudinal axis of the lead body to the fatigue-resistant zone, and extend from the fatigue-resistant zone substantially parallel to the longitudinal axis of the lead body to the proximal region.

9. The lead of claim 1, further comprising a first fixation element coupled to the lead body proximal to at least one of the at least one electrode, the first fixation element configured to anchor the lead to an anchor site.

10. The lead of claim 9, further comprising a second fixation element coupled to the lead body distal to the first fixation element, wherein the first fixation element is angled distally relative to the lead body and the second fixation element is angled proximally relative to the lead body in a deployed state, and wherein the first and second fixation elements are configured to sandwich the anchor site therebetween.

11. The lead of claim 10, wherein at least one of the at least one electrode is disposed between the first and second fixation elements.

12. The lead of claim 9, wherein the anchor site comprises muscle tissue associated with control of the lumbar spine.

13. The lead of claim 1, wherein the at least one electrode is configured to stimulate a dorsal ramus nerve, or fascicles thereof, that innervate a multifidus muscle.

14. A system for neuromuscular electrical stimulation of a patient, the system comprising:

the lead of claim 1; and a pulse generator configured to be electrically coupled to the at least one electrode via the at least one conductor.

15. The system of claim 14, wherein the pulse generator is implantable.

16. The system of claim 14, wherein the pulse generator is configured to deliver electrical stimulation to the nervous tissue associated with control of the lumbar spine via the at least one electrode.

17. A method for manufacturing an electrostimulation lead, the method comprising:

electrically coupling a distal end of at least one conductor to at least one electrode disposed at a distal region of the electrostimulation lead;

electrically coupling a proximal end of the at least one conductor to at least one contact disposed at a proximal region of the electrostimulation lead;

tightly winding a portion of the at least one conductor in a coiled configuration to form a fatigue-resistant zone of the electrostimulation lead, the fatigue-resistant zone configured to be disposed at a location within the patient that experiences fracture-inducing shear forces caused by movement of a patient's lower back muscles post-implantation; and encapsulating the at least one conductor with an insulated tube, wherein the at least one conductor comprises individual strands that extend in a straight configuration parallel to a longitudinal axis of the lead body outside of the fatigue-resistant zone, and wherein the individual strands of the at least one conductor are maintained in the coiled configuration within the fatigue-resistant zone and gradually transition towards the straight configuration in a semi-coiled configuration within a first transition portion proximal to the fatigue-resistant zone to thereby extend in the straight configuration outside of the fatigue-resistant zone towards the proximal region, and within a second transition portion distal to the fatigue-resistant zone to thereby extend in the straight configuration outside of the fatigue-resistant zone towards the distal region.

18. A method for implanting an electrostimulation lead within a patient, the method comprising:

selecting an electrostimulation lead having a proximal region, a distal region, a fatigue-resistant zone disposed between the proximal region and the distal region, and at least one conductor comprising individual strands that extend from the distal region to the proximal region in a straight configuration parallel to a longitudinal axis of the electrostimulation lead outside of the fatigue-resistant zone; and implanting the distal region of the electrostimulation lead adjacent to nervous tissue associated with control of a lumbar spine such that the fatigue-resistant zone of the electrostimulation lead is disposed at a location within the patient that experiences fracture-inducing shear forces caused by movement of the patient's lower back muscles post-implantation, wherein the individual strands of the at least one conductor are tightly wound in a coiled configuration within the fatigue-resistant zone to enhance fatigue-resistance at the fatigue-resistant zone, and wherein the individual strands of the at least one conductor are maintained in the coiled configuration within the fatigue-resistant zone and gradually transition towards the straight configuration in a semi-coiled configuration within a first transition portion proximal to the fatigue-resistant zone to thereby extend in the straight configuration outside of the fatigue-resistant zone towards the proximal region, and within a second transition portion distal to the fatigue-resistant zone to thereby extend in the straight configuration outside of the fatigue-resistant zone towards the distal region.

19. The method of claim 18, further comprising:

coupling the proximal region of the electrostimulation lead to a pulse generator; and delivering electrical stimulation from the pulse generator to the nervous tissue associated with control of the lumbar spine via at least one electrode disposed at the distal region of the electrostimulation lead.

20. The method of claim 18, further comprising implanting the pulse generator within the patient.

* * * * *